US012702313B2

(12) United States Patent
Ono et al.

(10) Patent No.: US 12,702,313 B2
(45) Date of Patent: Aug. 11, 2026

(54) BLOOD PRESSURE MEASUREMENT DEVICE

(71) Applicants: OMRON Corporation, Kyoto (JP); OMRON HEALTHCARE Co., Ltd., Kyoto (JP)

(72) Inventors: Takashi Ono, Kyoto (JP); Takanori Nishioka, Kyoto (JP)

(73) Assignees: OMRON CORPORATION, Kyoto (JP); OMRON HEALTHCARE CO., LTD., Kyoto (JP)

( * ) Notice: Subject to any disclaimer, the term of this patent is extended or adjusted under 35 U.S.C. 154(b) by 757 days.

(21) Appl. No.: 17/304,588

(22) Filed: Jun. 23, 2021

(65) Prior Publication Data

US 2021/0307631 A1 Oct. 7, 2021

Related U.S. Application Data

(63) Continuation of application No. PCT/JP2019/048039, filed on Dec. 9, 2019.

(30) Foreign Application Priority Data

Dec. 27, 2018 (JP) ............................ JP2018-246200

(51) Int. Cl.
*A61B 5/022* (2006.01)
*A61B 5/00* (2006.01)

(52) U.S. Cl.
CPC .......... *A61B 5/02233* (2013.01); *A61B 5/681* (2013.01)

(58) Field of Classification Search
CPC . A61B 5/02141; A61B 5/02233; A61B 5/681; A61B 5/6824; A61B 5/6844;
(Continued)

(56) References Cited

U.S. PATENT DOCUMENTS 6,344,025 B1 * 2/2002 Inagaki .............. A61B 5/02233 600/490
2004/0243009 A1 * 12/2004 Tanaka .............. A61B 5/02438 600/503

(Continued)

FOREIGN PATENT DOCUMENTS

CN 108324261 A * 7/2018 ........... A61B 5/0225
JP S63200144 A 8/1988

(Continued)

OTHER PUBLICATIONS

WO-2018163573-A1 English Translation (Year: 2018).*

(Continued)

*Primary Examiner* — Aurelie H Tu
*Assistant Examiner* — Andrew E Hoffpauir
(74) *Attorney, Agent, or Firm* — Wenderoth, Lind & Ponack, L.L.P.

(57) ABSTRACT

A blood pressure measurement device includes a curler, a cuff structure on an inner surface of the curler, a case including a tubular shaped outer case and a rear cover fixed to an end portion on a living body side of the outer case and the curler, a portion of the rear cover facing the curler being open, and the rear cover and curler covering the end portion on the living body side of the outer case, a base portion housed in the case, a first sealing member between the rear cover and the curler, that is configured to seal between the rear cover and the curler, and a second sealing member having a higher sealing property than the first sealing member, between an inner circumferential surface of the outer case and the base portion, that is configured to seal between the inner circumferential surface and the base portion.

7 Claims, 31 Drawing Sheets

(58) Field of Classification Search

CPC .......... A61B 2562/12; A61B 2562/164; A61B 2562/18; A61B 5/0223; A61B 5/022; A61B 5/02438; A61B 5/02225; A61B 5/0235; A61B 5/02427; A61B 5/6831; A61B 5/021; A61B 5/332; A61B 5/02422; A61B 5/02444; A61B 5/025; A61B 2560/04; A61B 2560/0425; A61B 2560/0462

USPC .......................... 600/485, 499, 503; 606/202

See application file for complete search history.

(56) References Cited

U.S. PATENT DOCUMENTS

| | | | | |
|---|---|---|---|---|
| 2008/0312544 | A1* | 12/2008 | Mochizuki | A61B 5/022 600/492 |
| 2009/0054794 | A1* | 2/2009 | Shirasaki | A61B 5/02141 600/490 |
| 2014/0268522 | A1* | 9/2014 | Tanaka | A61B 5/0295 361/679.01 |
| 2017/0092896 | A1* | 3/2017 | Nakamura | H10K 50/8445 |
| 2017/0215744 | A1* | 8/2017 | Kawamura | A61B 5/0235 |
| 2019/0061318 | A1* | 2/2019 | Jung | G02F 1/1335 |
| 2019/0099095 | A1* | 4/2019 | Zhang | A61B 5/02241 |
| 2020/0085319 | A1* | 3/2020 | Lin | F04B 53/10 |
| 2021/0106278 | A1* | 4/2021 | Quinn | G06F 1/16 |

FOREIGN PATENT DOCUMENTS

| | | | | |
|---|---|---|---|---|
| JP | H0611701 | A | 1/1994 | |
| JP | 2015-119911 | A | 7/2015 | |
| WO | 2017/203957 | A1 | 11/2017 | |
| WO | WO-2018163573 | A1 * | 9/2018 | A61B 5/02141 |
| WO | 2018/179645 | A1 | 10/2018 | |

OTHER PUBLICATIONS

CN 108324261 A English Translation (Year: 2018).*

Translation of International Preliminary Report on Patentability and Written Opinion of the International Searching Authority issued Jul. 8, 2021 in International (PCT) Application No. PCT/JP2019/048039.

* cited by examiner

[FIG. 1]
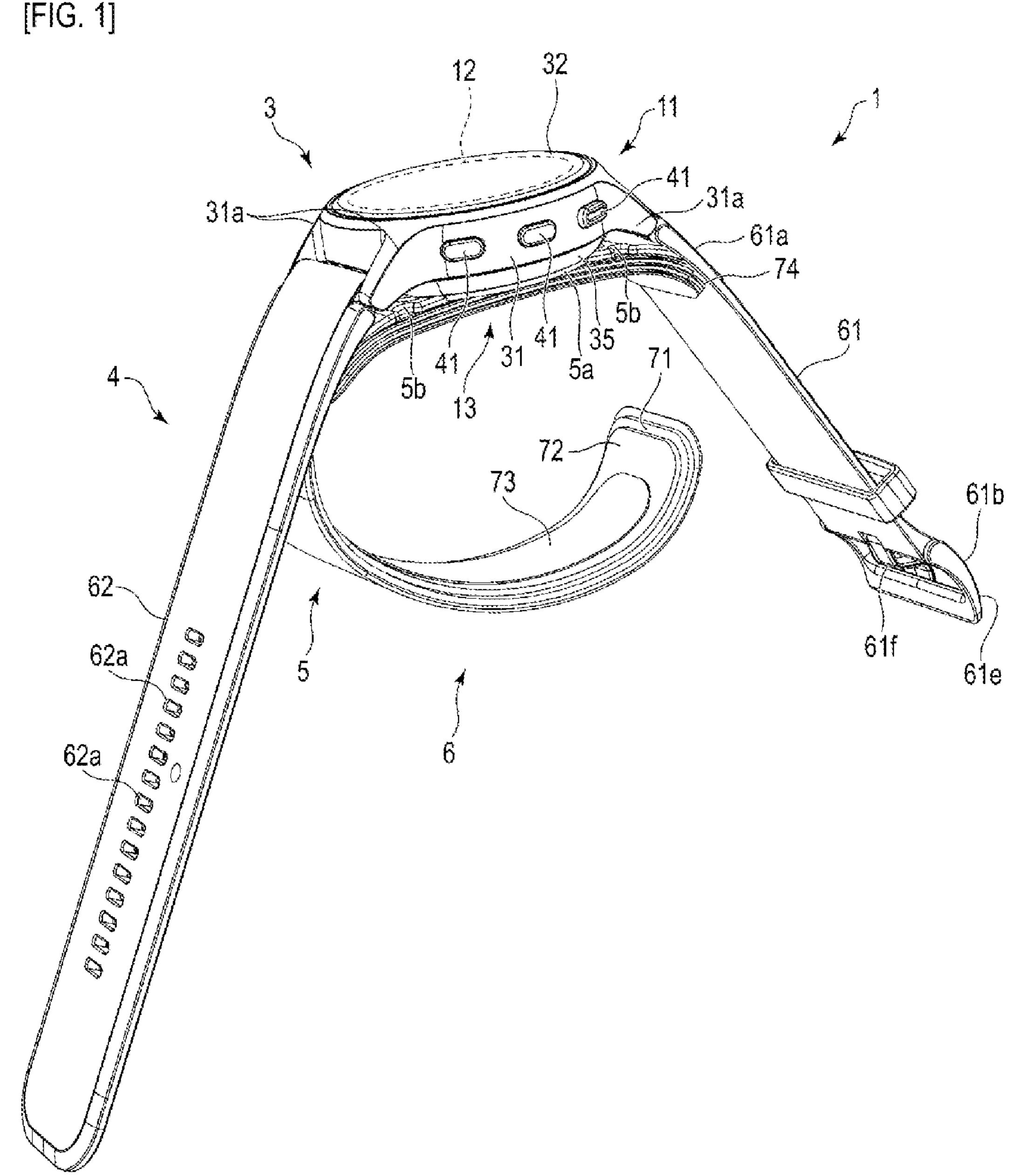

[FIG. 2]
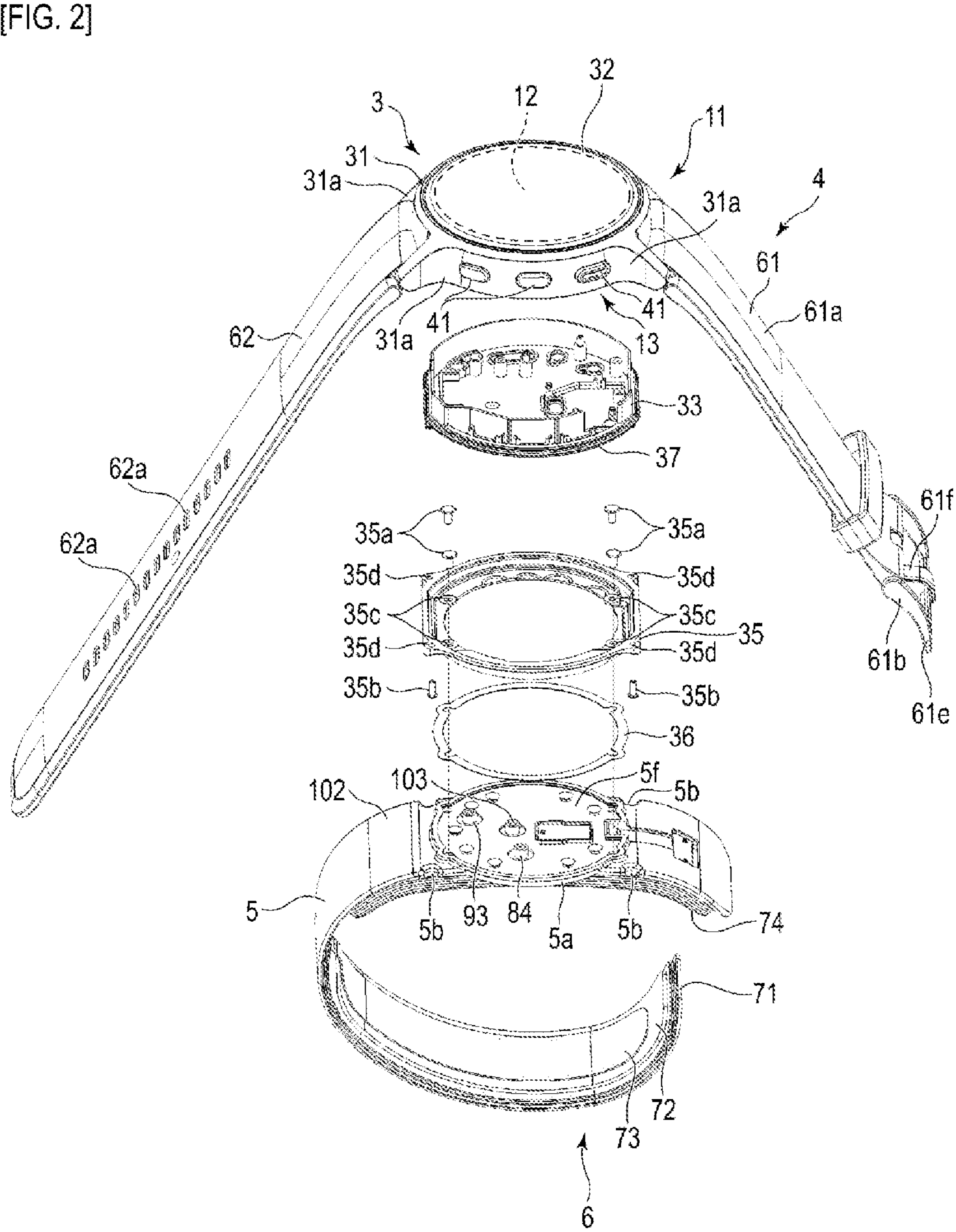

[FIG. 3]
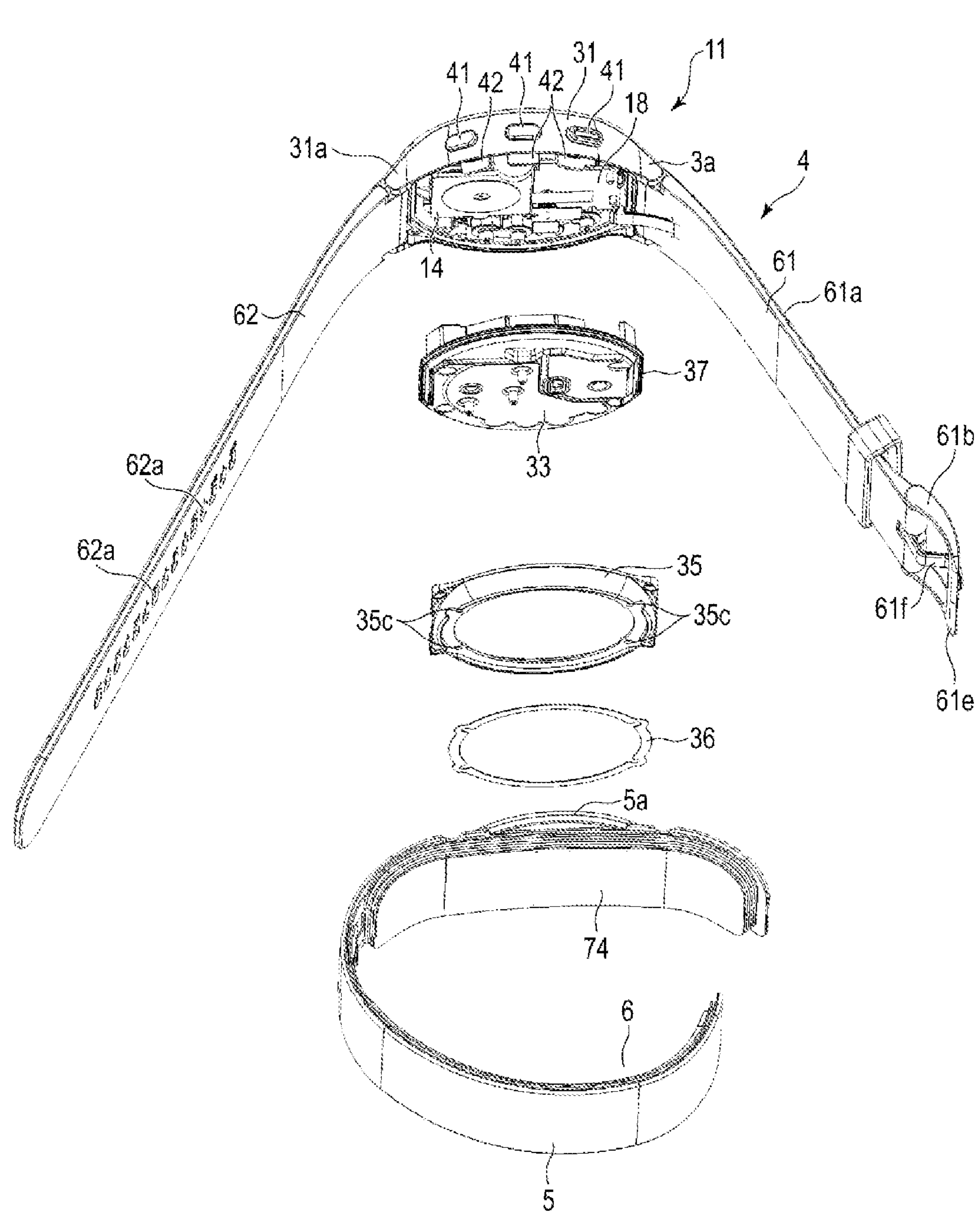

[FIG. 4]
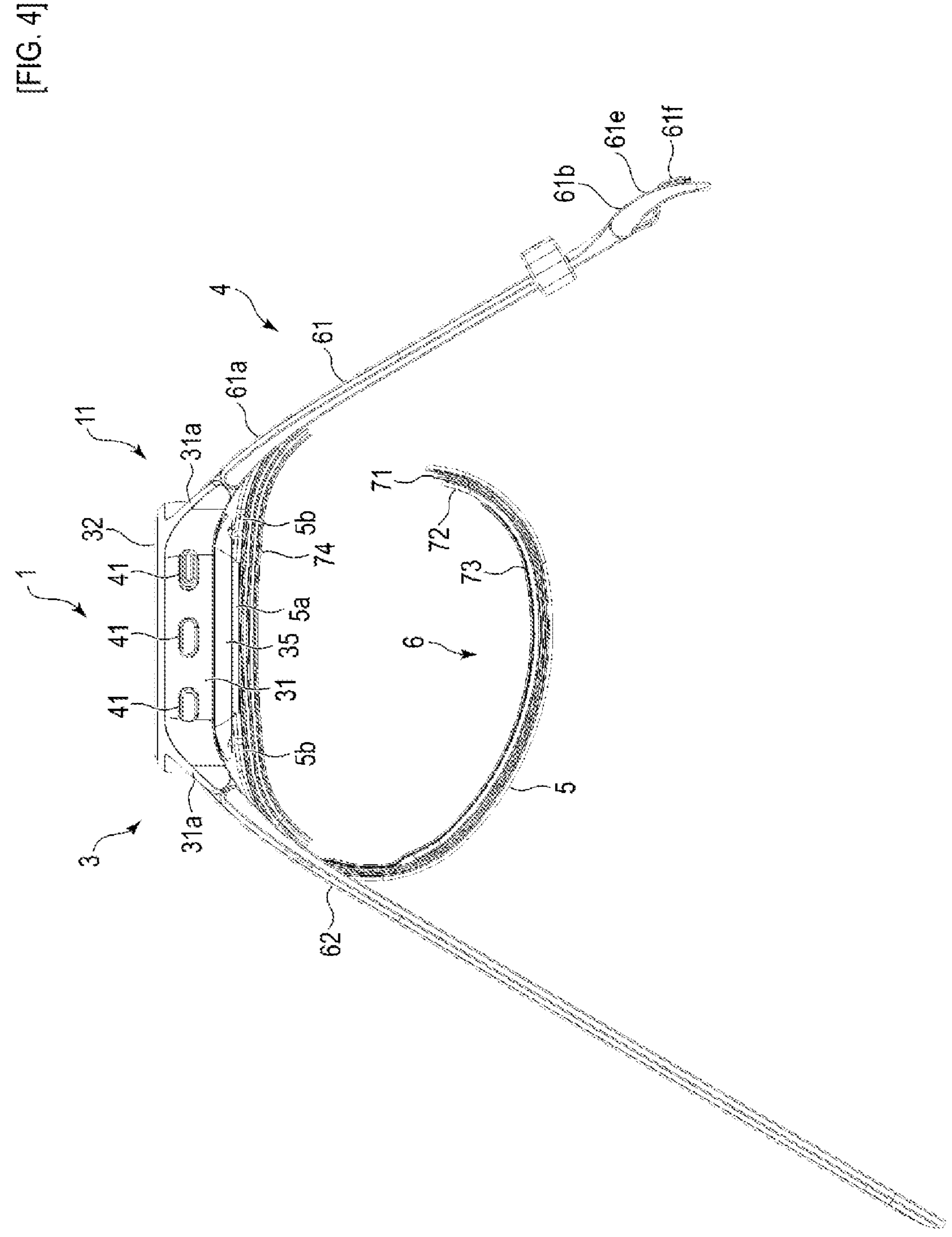

[FIG. 5]
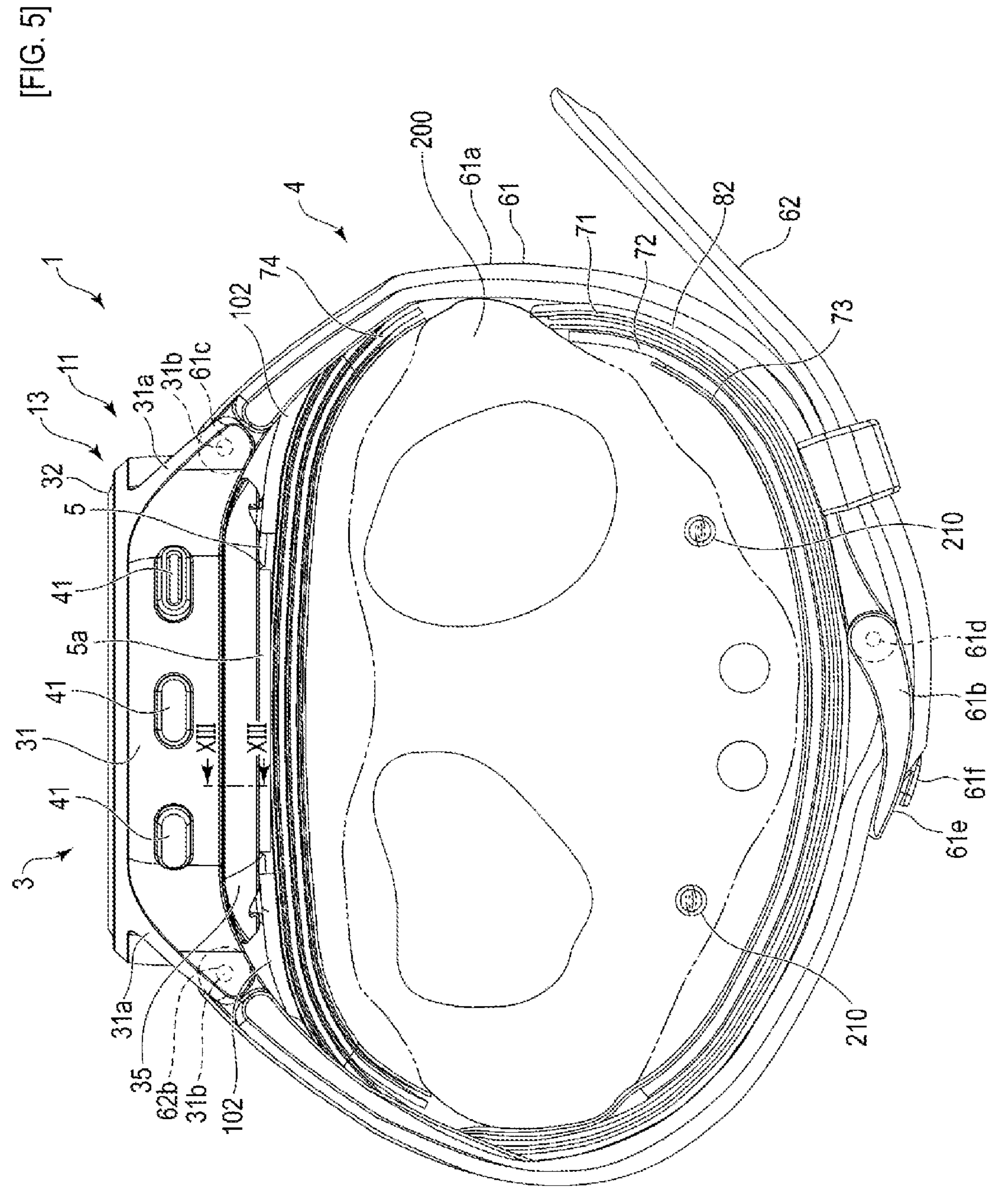

[FIG. 6]
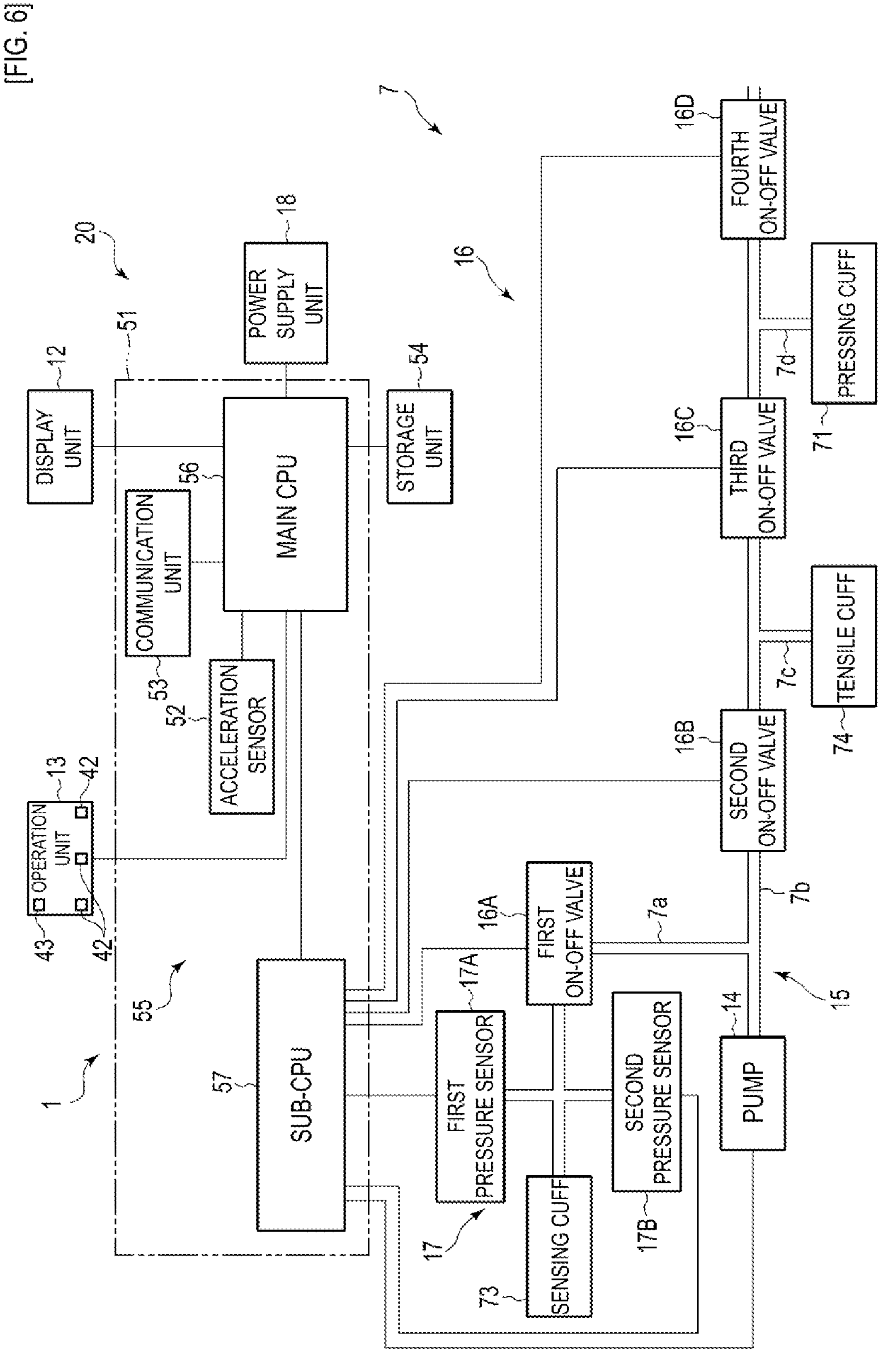

[FIG. 7]

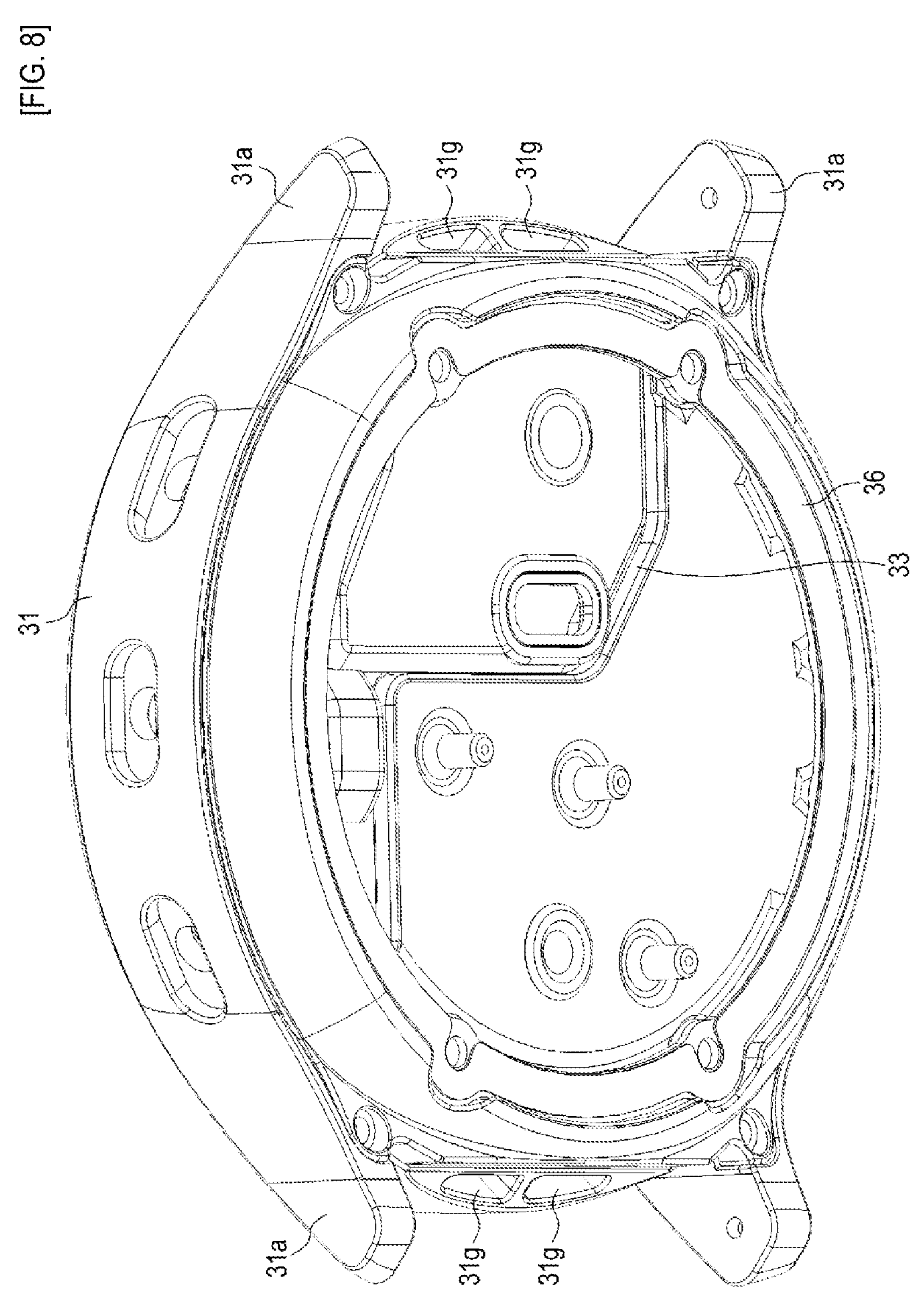
[FIG. 8]
31a
31g
31g
31a
36
33
31
31a
31g
31g

[FIG. 9]
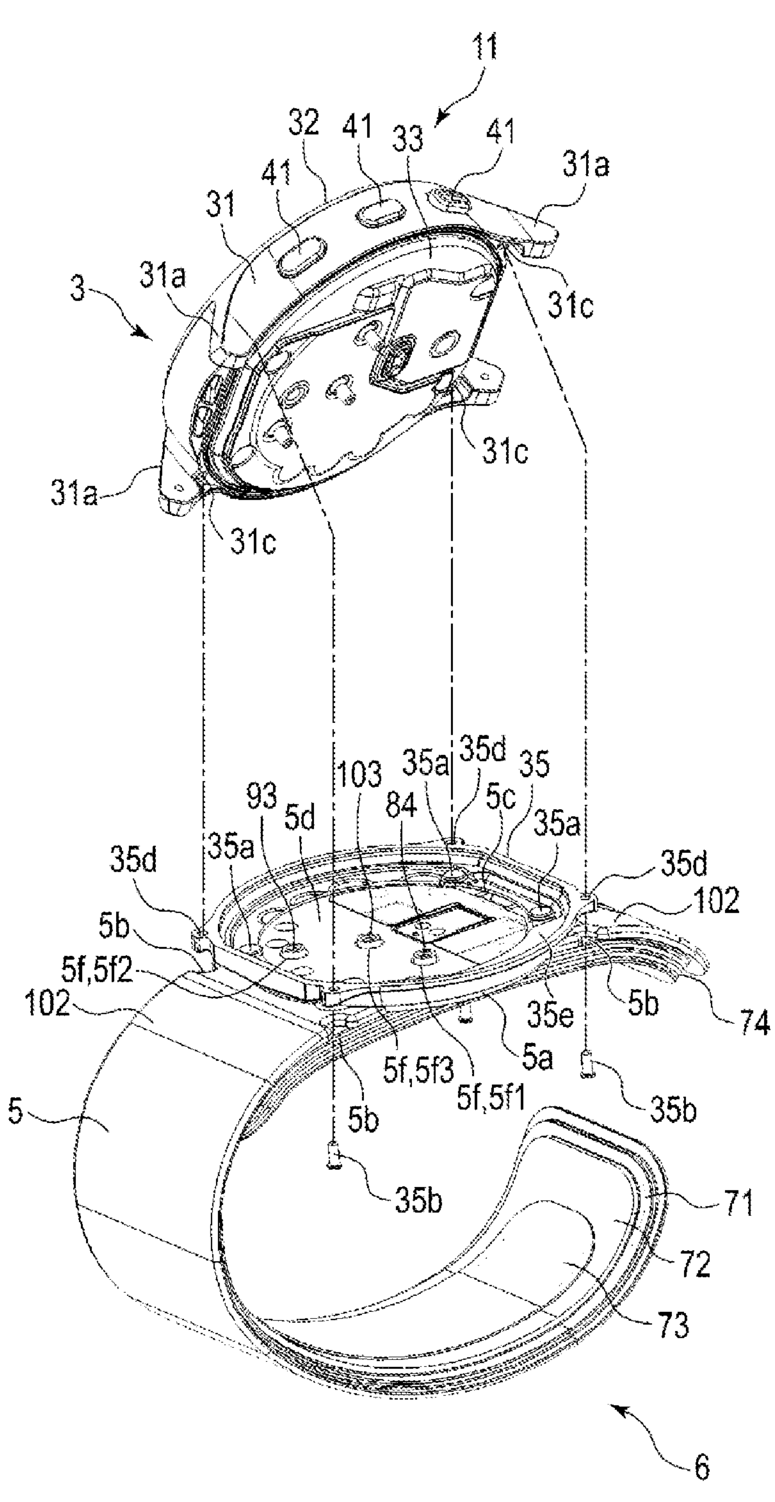

[FIG. 10]
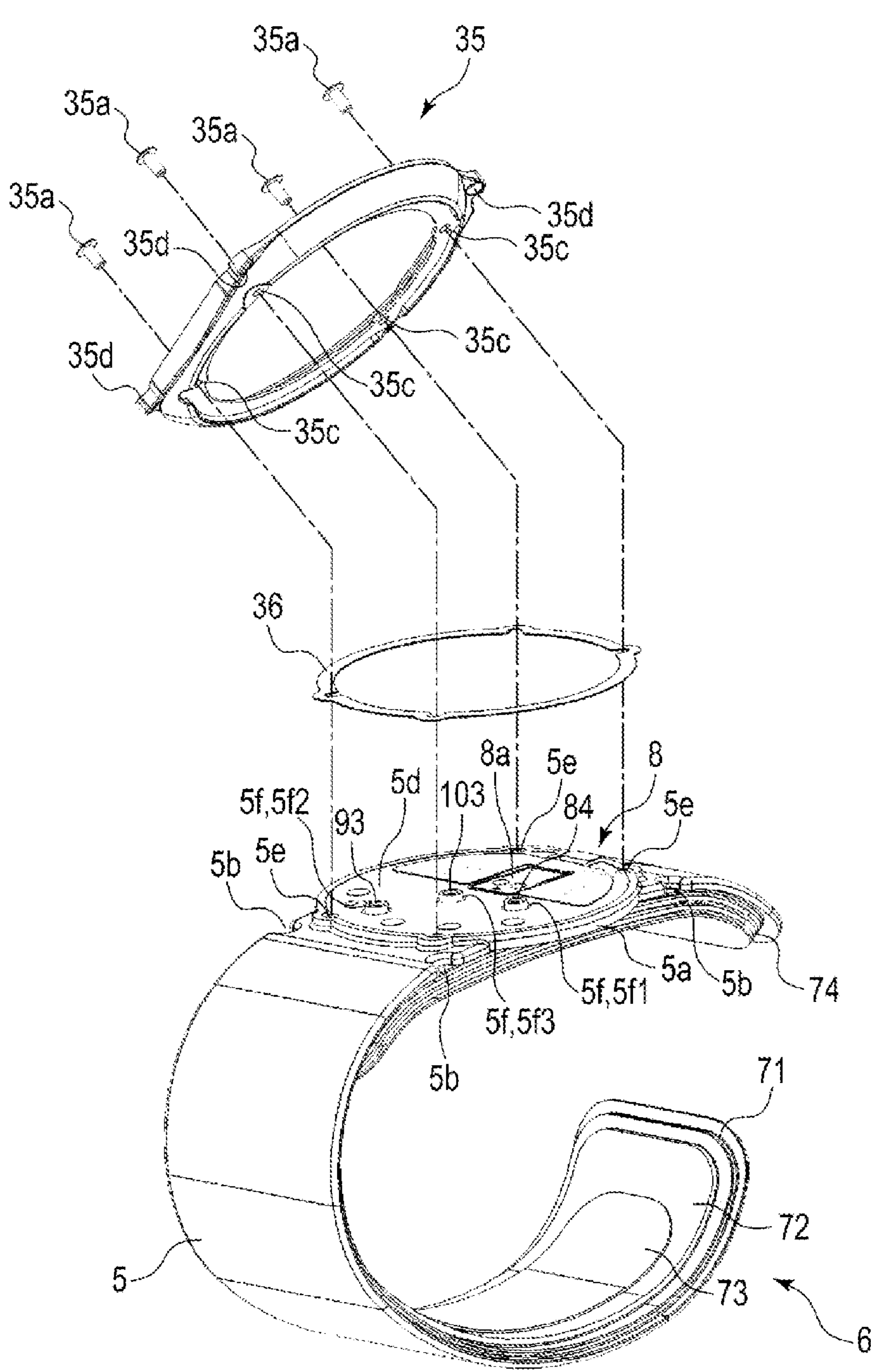

[FIG. 11]
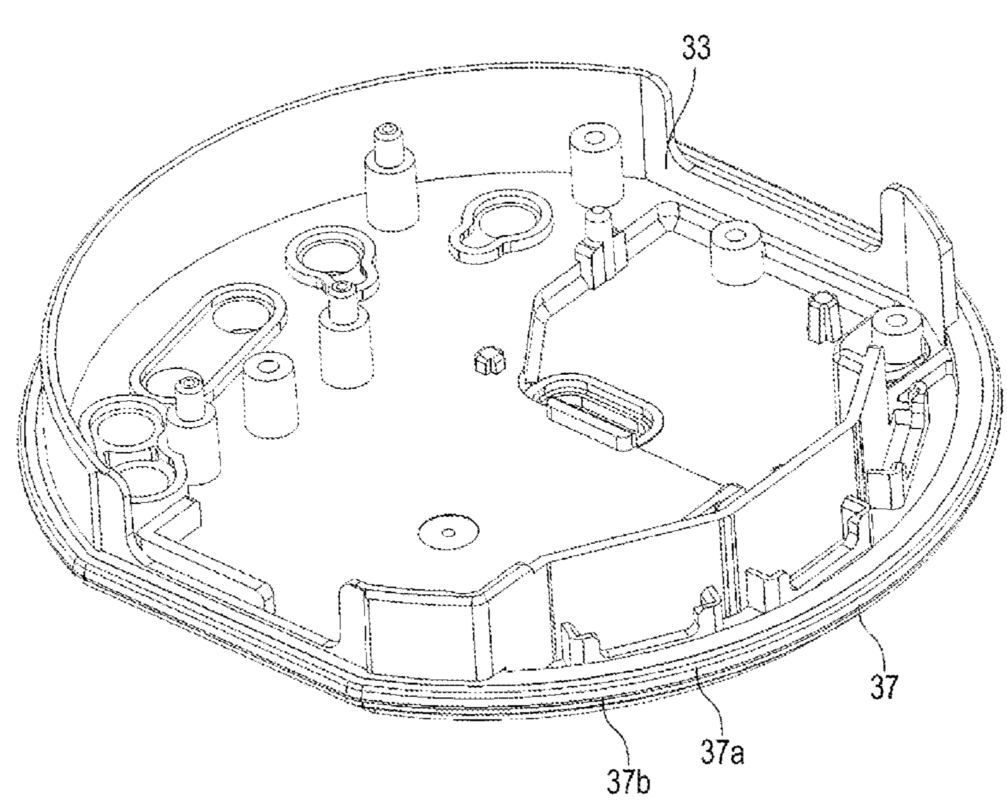

[FIG. 12]
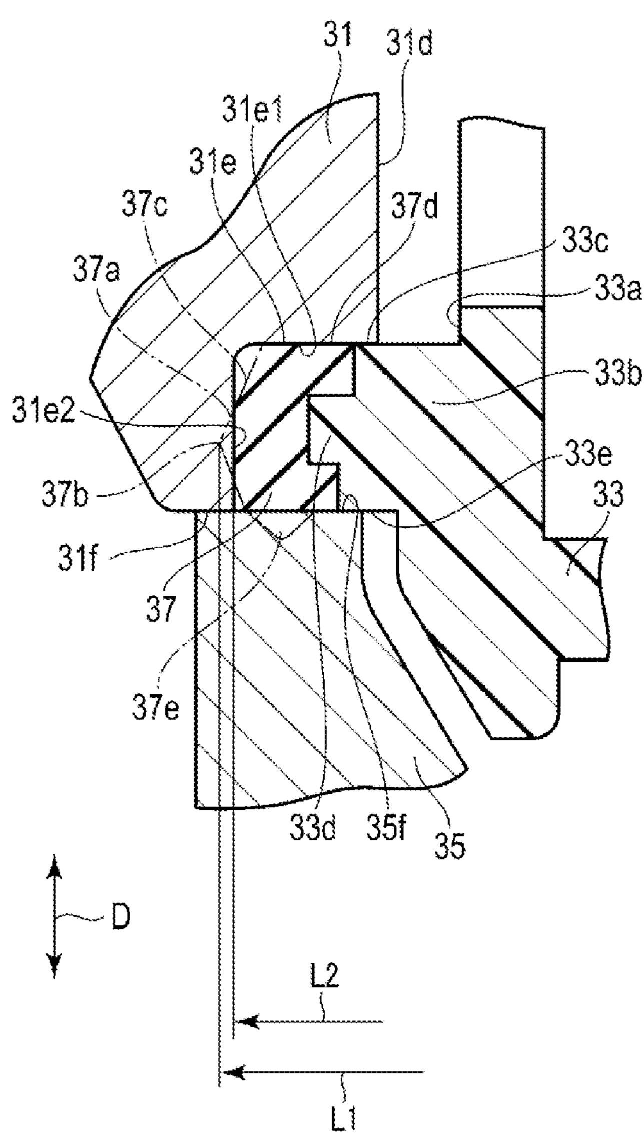

[FIG. 13]
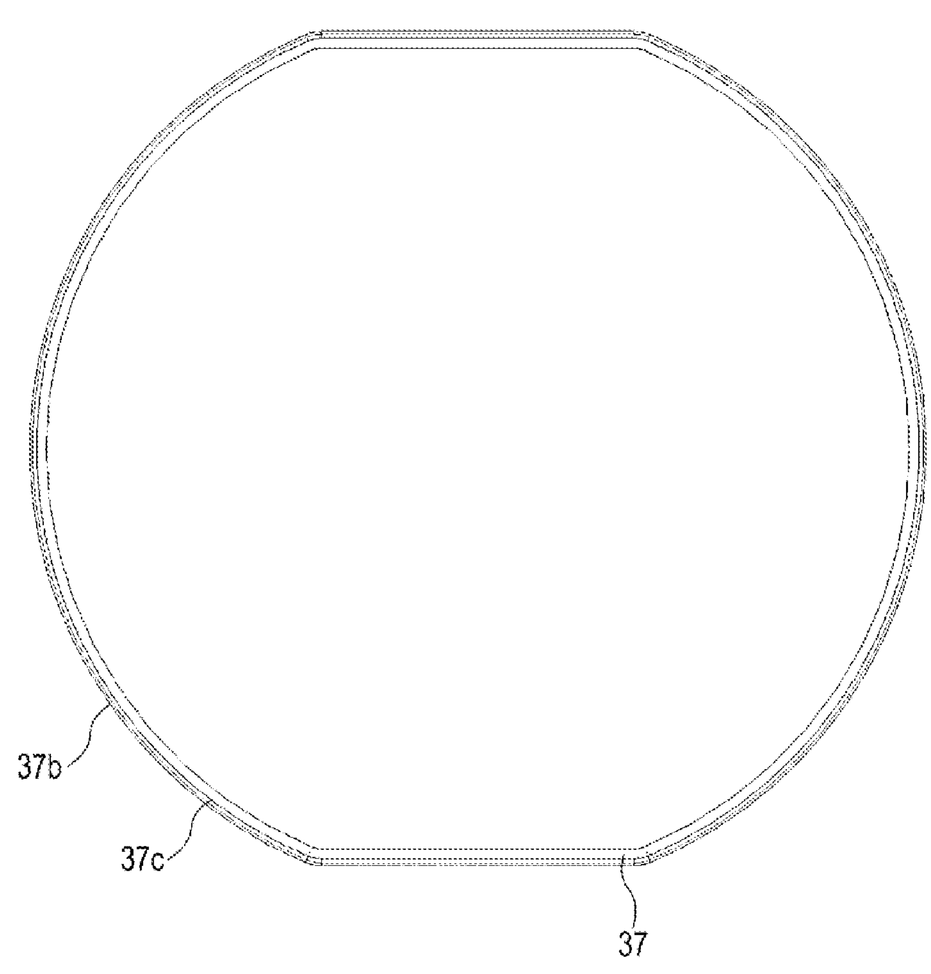

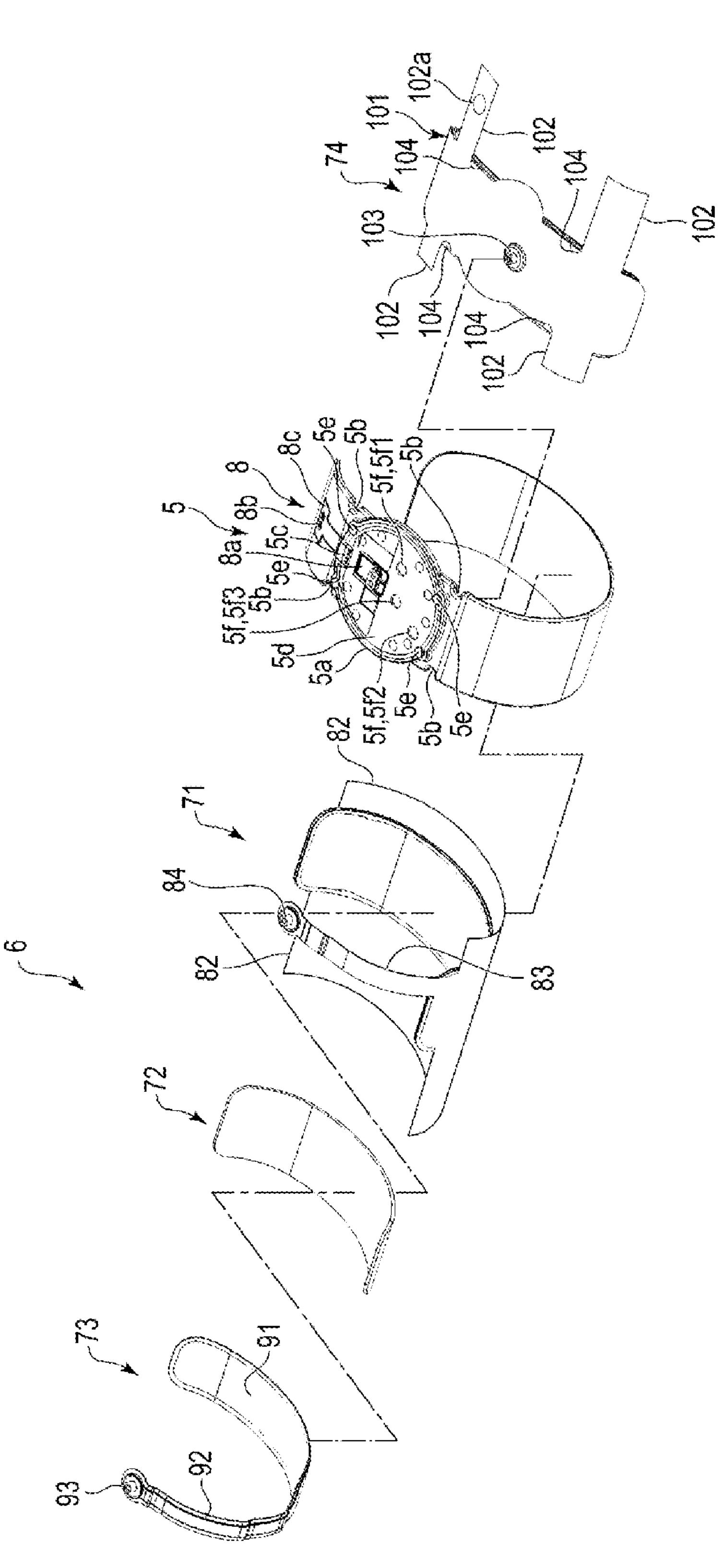
[FIG. 14]
6
71
72
73
74
5
8
8a
8b
8c
5a
5b
5c
5d
5e
5f,5f1
5f,5f2
5f,5f3
82
83
84
91
92
93
101
102
102a
103
104

[FIG. 15]
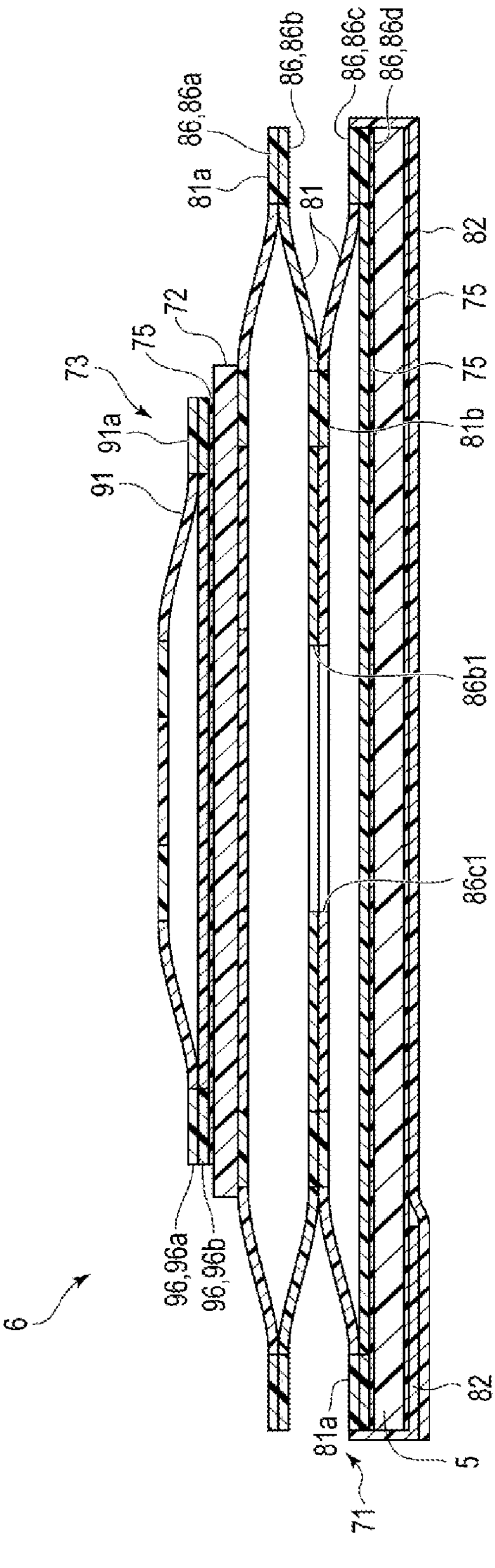

[FIG. 16]
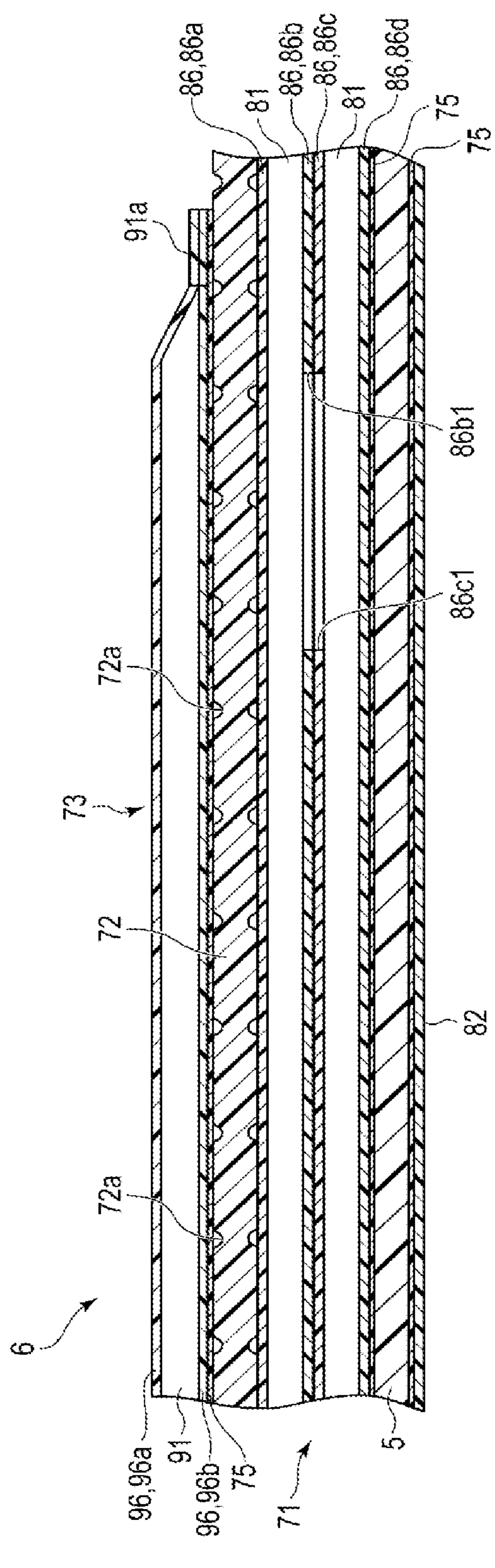

[FIG. 17]
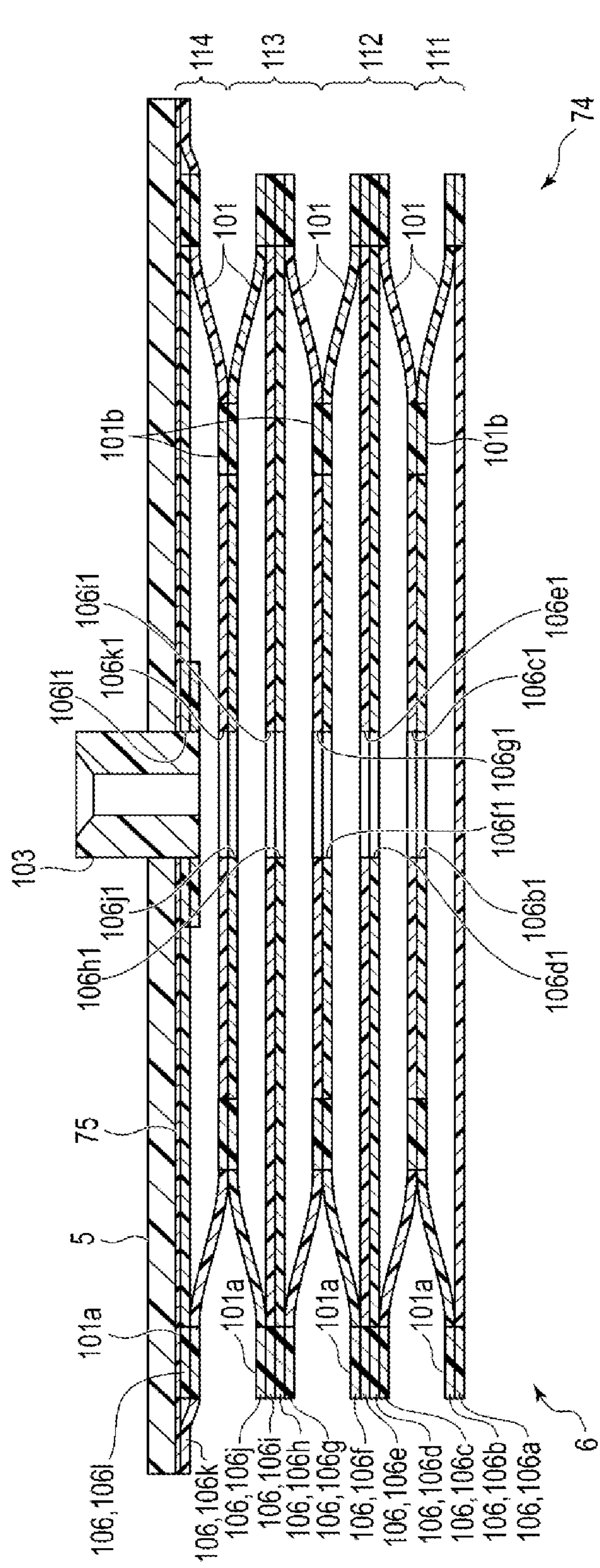

[FIG. 18]
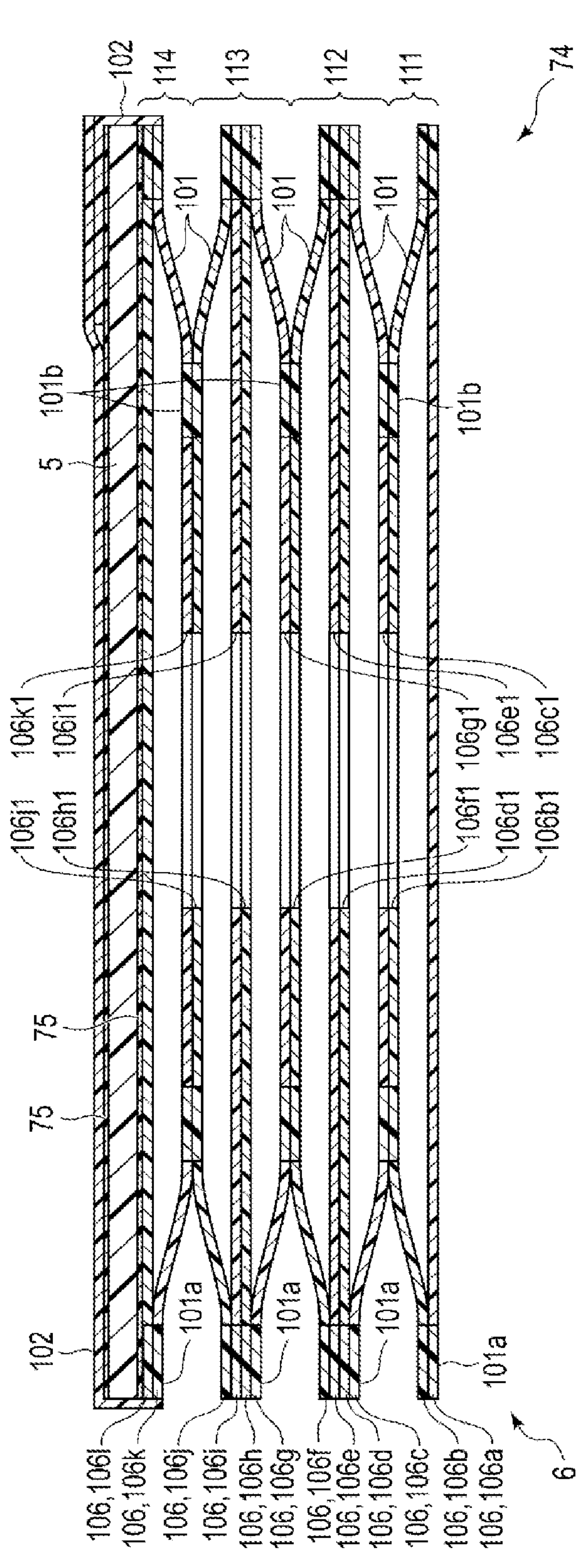

[FIG. 19]
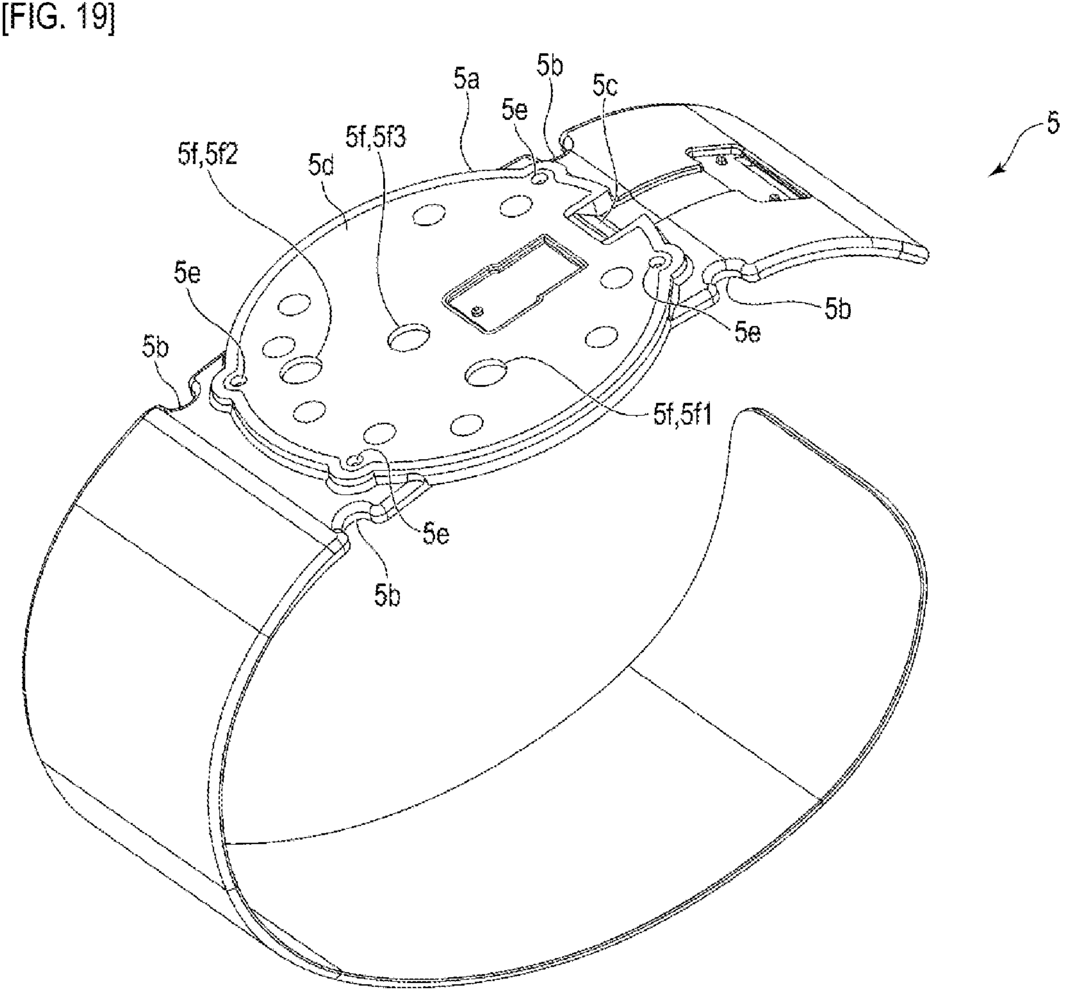

[FIG. 20]
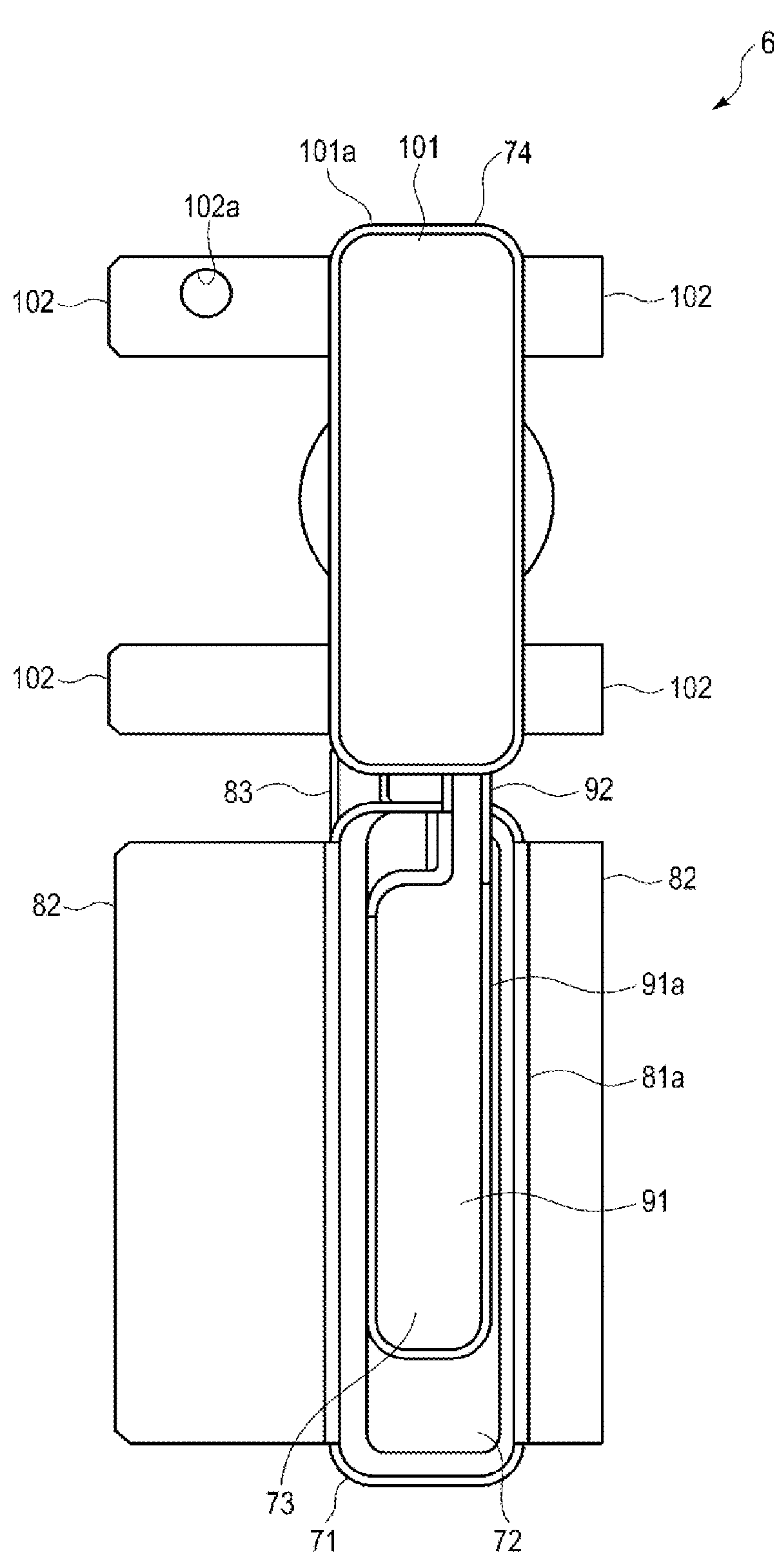

[FIG. 21]
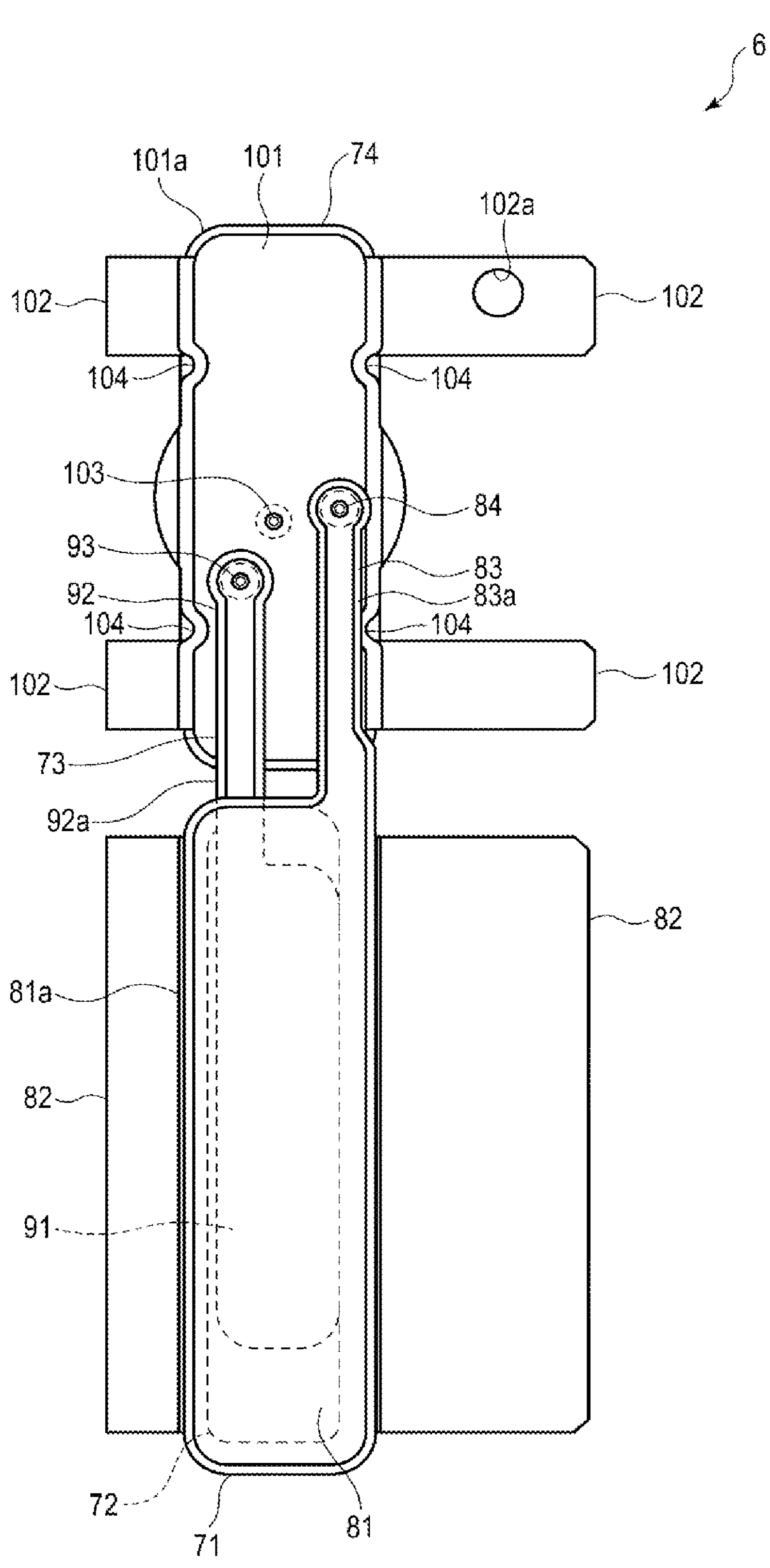

[FIG. 22]
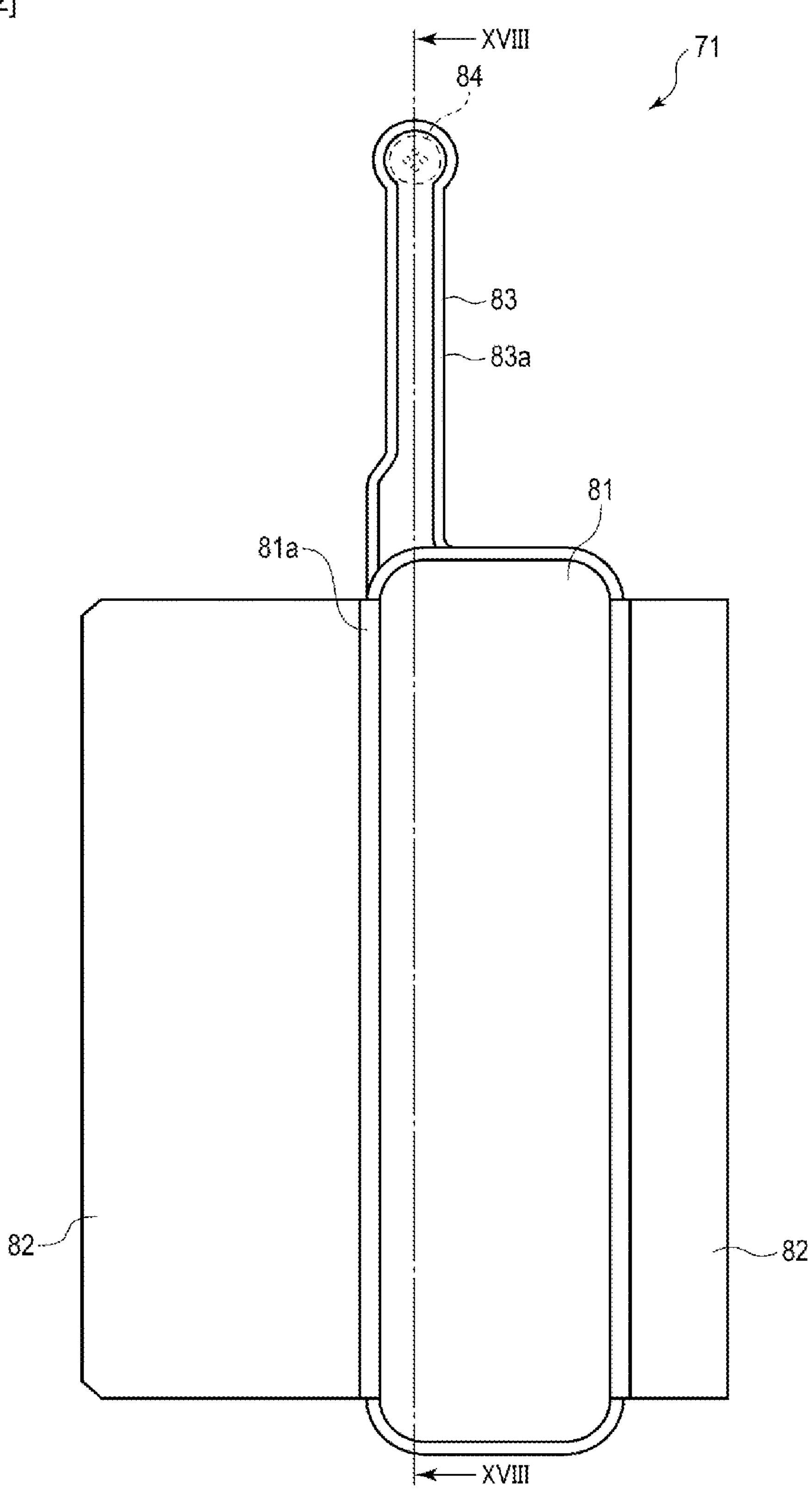

[FIG. 23]
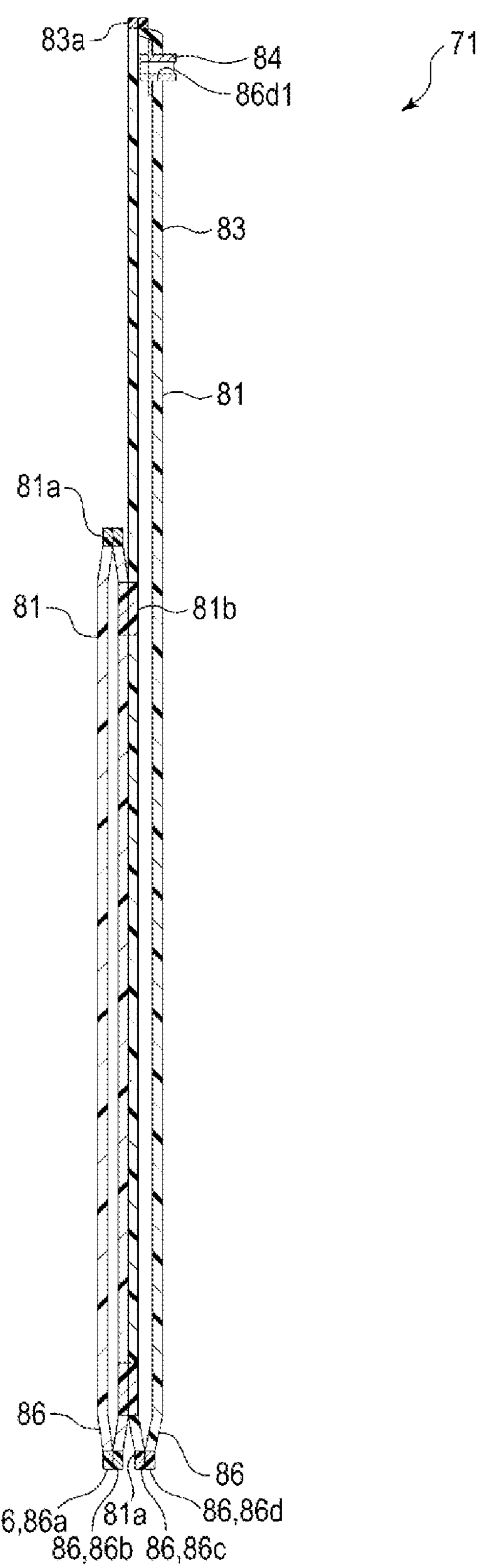

[FIG. 24]
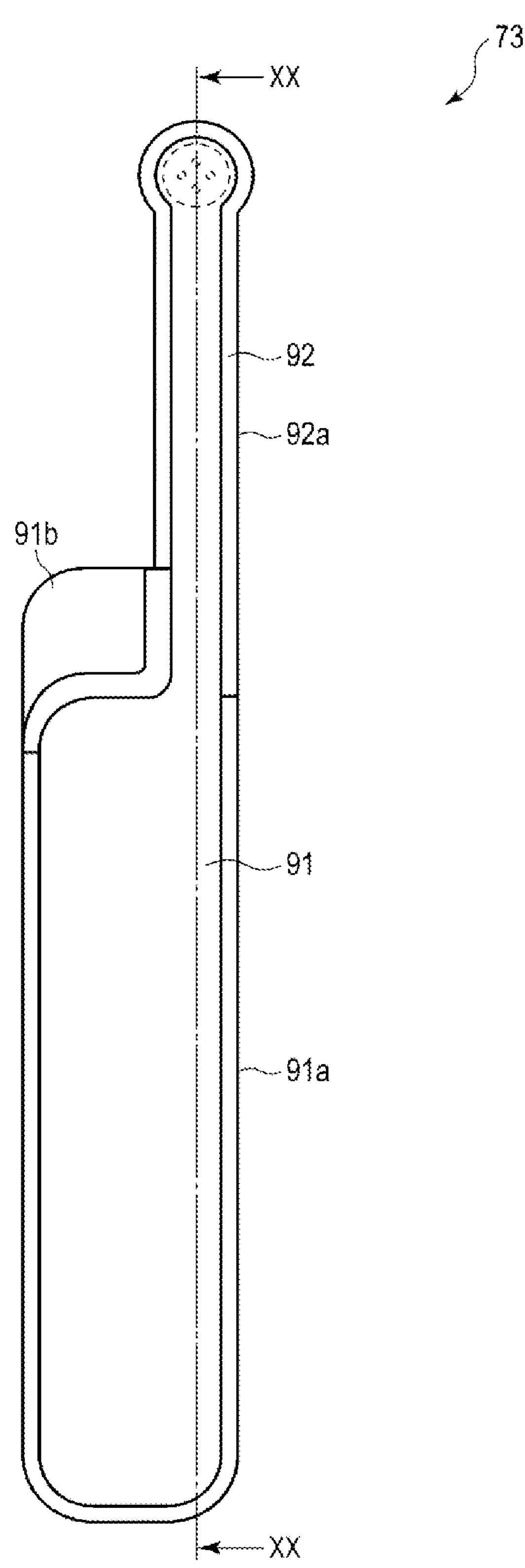

[FIG. 25]
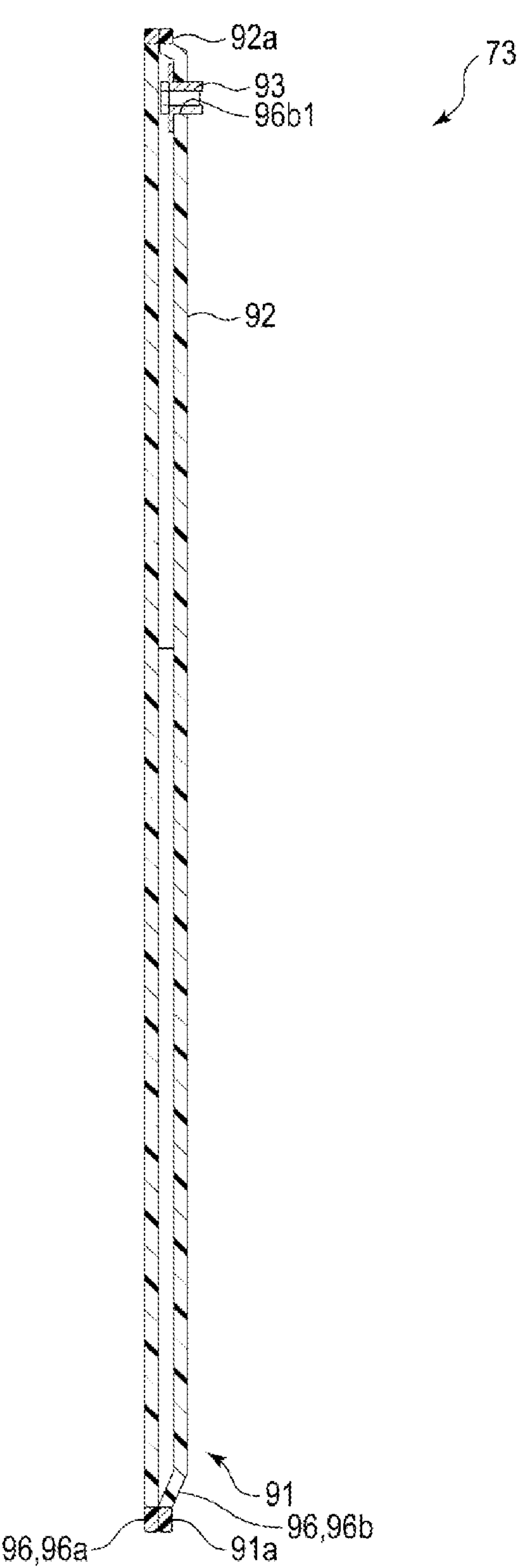

[FIG. 26]
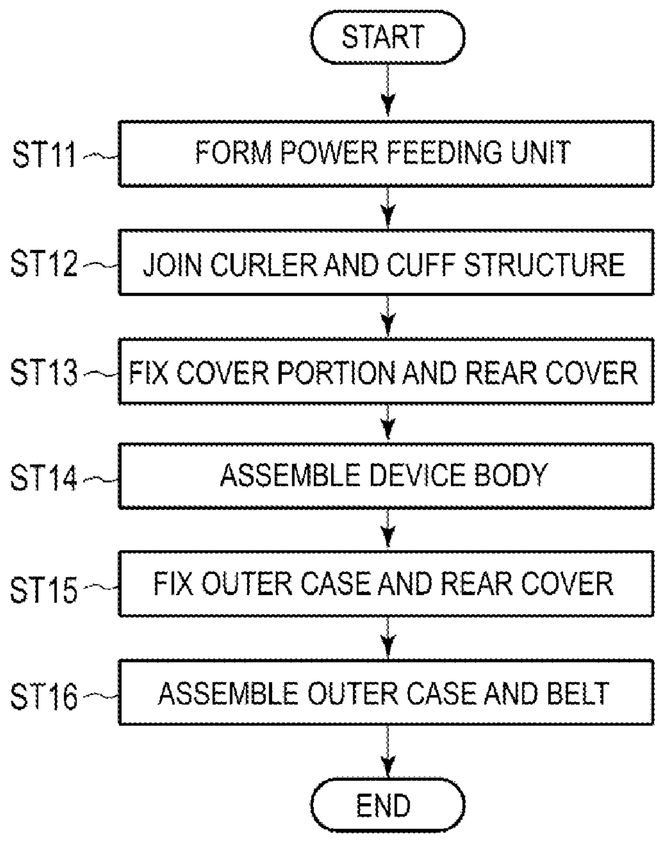

[FIG. 27]
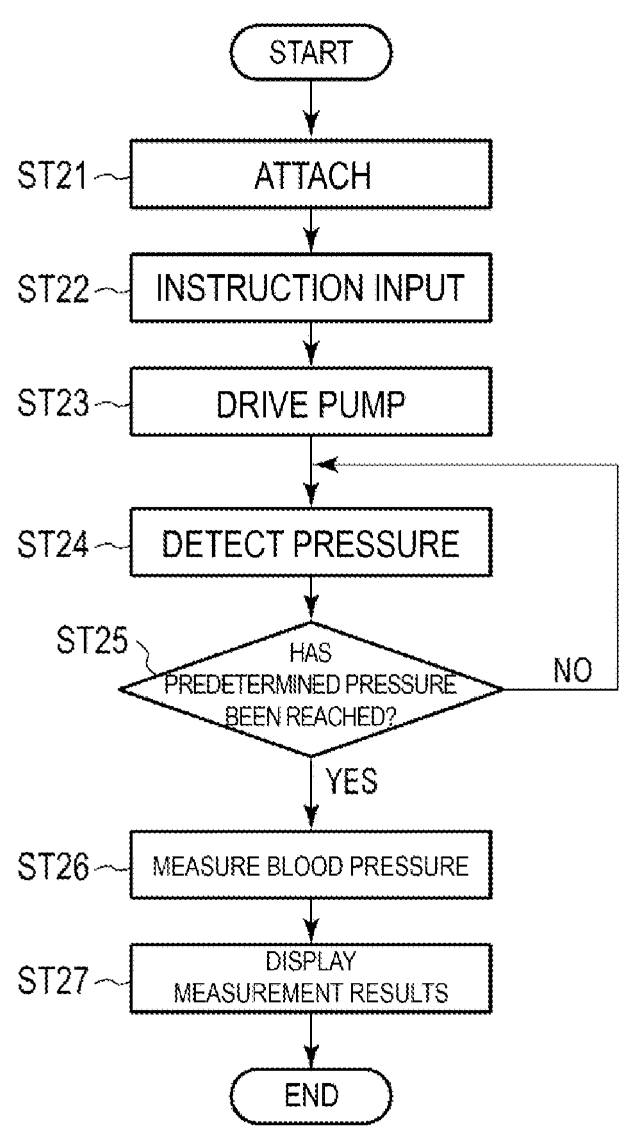

[FIG. 28]
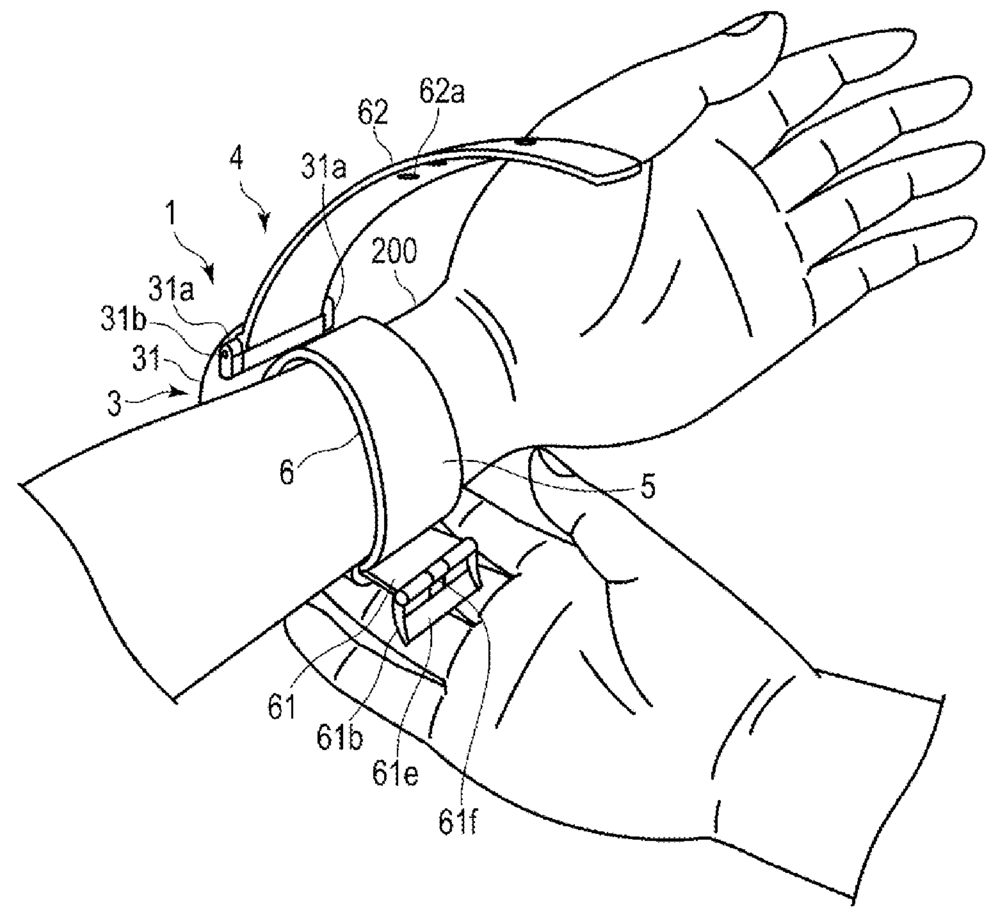

[FIG. 29]
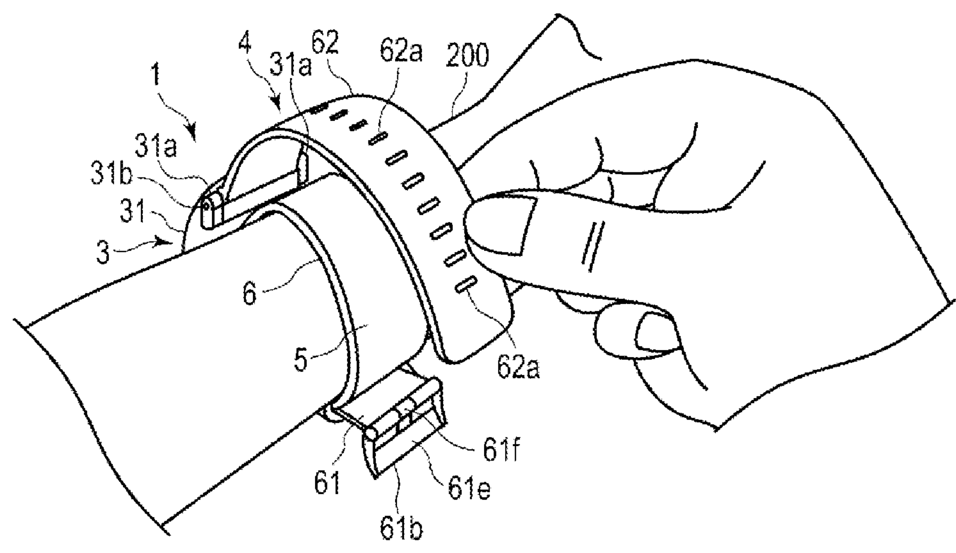
[FIG. 30]
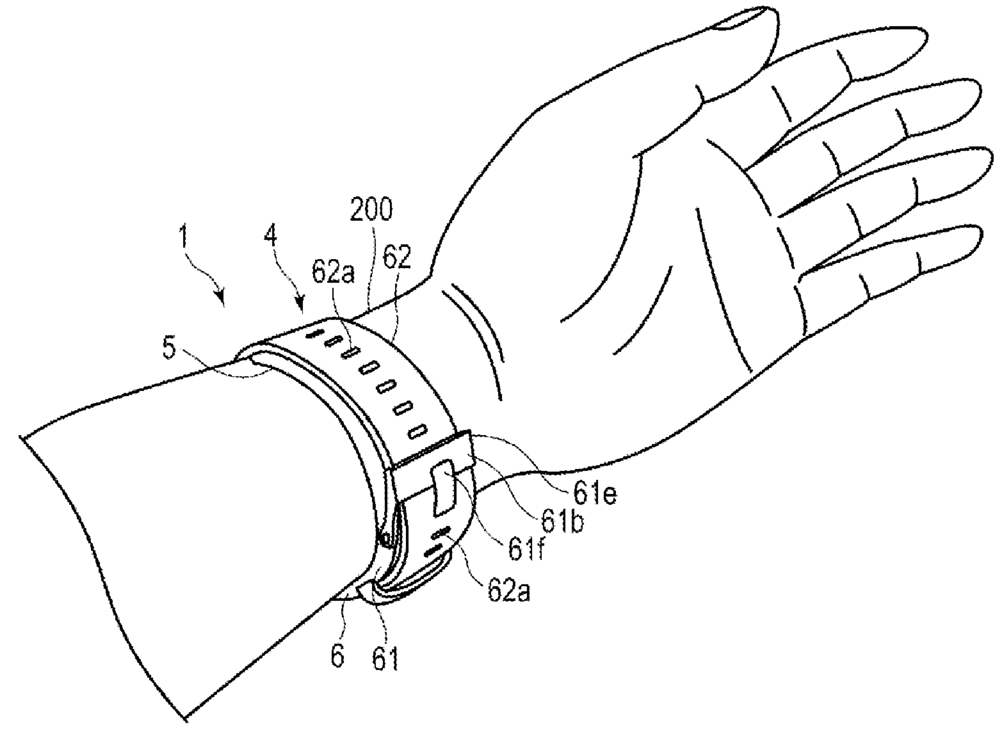

[FIG. 31]
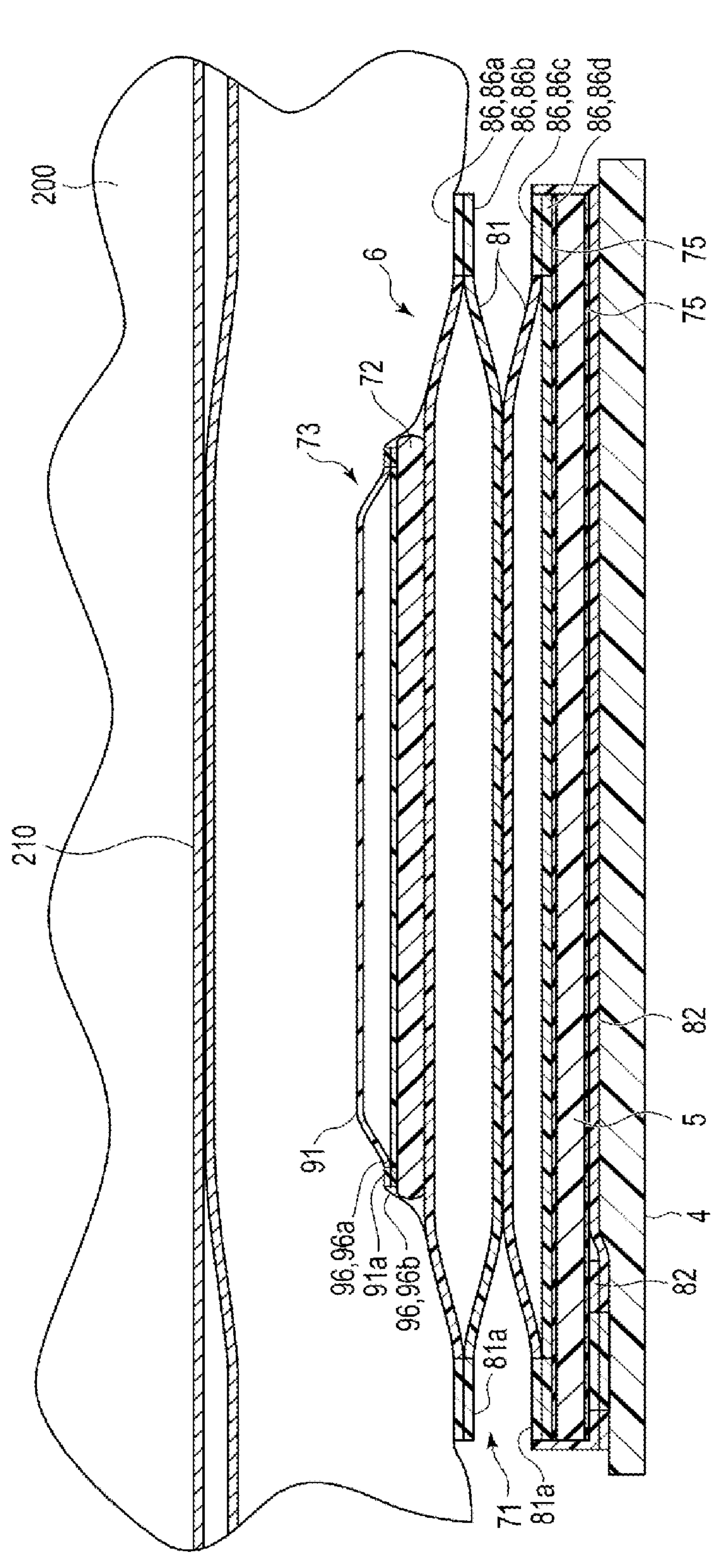

[FIG. 32]
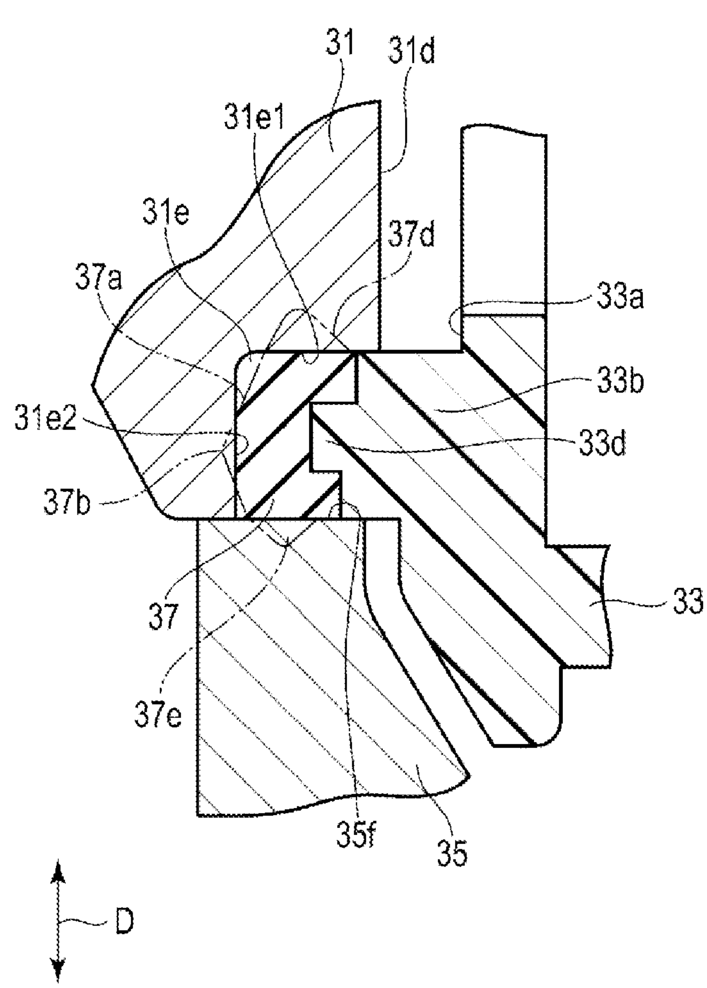

BLOOD PRESSURE MEASUREMENT DEVICE

CROSS-REFERENCE TO RELATED APPLICATIONS

This application is the U.S. national stage application filed pursuant to 35 U.S.C. 365 (c) and 120 as a continuation of International Patent Application No. PCT/JP2019/048039, filed Dec. 9, 2019, which application claims priority to Japan Patent Application No. 2018-246200, filed Dec. 27, 2018, which applications are incorporated herein by reference in their entireties.

TECHNICAL FIELD

The present invention relates to a blood pressure measurement device for measuring blood pressure.

BACKGROUND ART

In recent years, blood pressure measurement devices for measuring blood pressure are being used to monitor health status at home, as well as in medical facilities. A blood pressure measurement device detects vibration of the artery wall to measure blood pressure by, for example, inflating and contracting a cuff wrapped around the upper arm or the wrist of a living body and detecting the pressure of the cuff using a pressure sensor.

As such a blood pressure measurement device, for example, a so-called integral type is known in which a cuff is integrated with a device body supplying a fluid to the cuff. Known examples of an integral type blood pressure measurement device include the blood pressure measurement devices described in JP H06-011701 A and JP S63-200144 A in which a cuff is disposed on the inner side of a belt and a flow path connecting from a pump disposed inside a device body to the cuff is provided (see Patent Document 1 and Patent Document 2, for example).

Also, technology is known that uses a curler between a belt and a cuff to bring the inflated cuff to be close contact with the wrist. Such blood pressure measurement devices inflate the cuff after the cuff is brought into close contact with the wrist by the belt and the curler to suitably occlude the blood vessel when the cuff is inflated.

CITATION LIST

Patent Literature

Patent Document 1: JP H06-011701 A
Patent Document 2: JP S63-200144 A

SUMMARY OF INVENTION

Technical Problem

The blood pressure measurement device described above needs to be configured to allow the cuff to be removed at the time of failure or maintenance of the cuff. Also, blood pressure measurement devices are being designed as wearable devices attached on the wrist, and thus there is a demand to have a waterproof function.

In light of this, an object of the present invention is to provide a blood pressure measurement device with a replaceable cuff and the waterproof function.

Solution to Problem

According to an aspect, a blood pressure measurement device is provided which is attachable to a living body and includes, a curler, a cuff disposed on an inner surface of the curler, a case including an outer case having a tubular shape and a rear cover fixed to an end portion on a living body side of the outer case and the curler, a portion of the rear cover facing the curler being open, and the rear cover covering, together with the curler, the end portion on the living body side of the outer case, a base portion housed in the case, a first sealing member provided between the rear cover and the curler, the first sealing member being configured to seal between the rear cover and the curler, and a second sealing member provided between an inner circumferential surface of the outer case and the base portion, the second sealing member being constituted in an annular shape that seals between the inner circumferential surface and the base portion and seals between the rear cover and the base portion, and the second sealing member having a higher sealing property than the first sealing member.

Here, the living body is the wrist, for example.

According to this aspect, the configuration includes the first sealing member and the second sealing member. This gives the blood pressure measurement device a high sealing property. Furthermore, with the two level structure including the first sealing member and the second sealing member functioning as a waterproof structure for inside the case, the sealing property required for the blood pressure measurement device can be satisfied by the combined sealing properties of the first sealing member and the second sealing member, allowing the individual sealing properties of the first sealing member and the second sealing member to be set not as high. Thus, the first sealing member and the second sealing member are not made as a seal with a complex mechanism, for example. As a result, the curler can be detached from the rear lid, and the cuff can be replaced. Furthermore, even in a case where the first sealing member needs to be replaced due to the curler being detached from the rear cover during such as maintenance or cuff replacement, the cost of the replacement can be kept low.

In the blood pressure measurement device according to the one aspect described above, the blood pressure measurement device is provided in which the outer case includes a first abutting portion, and the base portion includes a second abutting portion configured to abut on the first abutting portion in an axial direction of the outer case.

According to this aspect, misalignment of the outer case and the base portion can be prevented.

In the blood pressure measurement device according to the one aspect described above, the blood pressure measurement device is provided in which the first sealing member is constituted by a double-sided tape.

According to this aspect, the first sealing member can have a simple configuration. Also, by using the first sealing member itself to fix the curler to the rear cover, the curler and the rear cover can be strongly fixed. Furthermore, the replacement work of the first sealing member can be made simple, and the cost of replacing the first sealing member can be kept low.

In the blood pressure measurement device according to the one aspect described above, the blood pressure measurement device is provided in which the second sealing member is integrally formed with the base portion.

According to this aspect, the second sealing member can be prevented from falling off from the base portion.

In the blood pressure measurement device according to the one aspect described above, the blood pressure measurement device is provided in which, the second sealing member in a pre-deformation state, is formed with an intermediate portion, in an axial direction of the outer case, of an outer circumferential surface of the second sealing member having a larger diameter than other portions.

According to this aspect, the sealing properties of the second sealing member and the inner circumferential surface of the outer case can be improved.

In the blood pressure measurement device according to the one aspect described above, the blood pressure measurement device is provided in which, an outer circumferential surface of the base portion includes an annular protrusion portion disposed inside the second sealing member protruding toward an inner circumferential surface of the outer case.

According to this aspect, the second sealing member can be further prevented from falling off from the base portion.

In the blood pressure measurement device according to the one aspect described above, the blood pressure measurement device is provided in which, an intermediate portion in a radial direction of an end surface on the living body side of the second sealing member protrudes further to the living body side than an end on the living body side of the outer case, in a state before the rear cover is fixed to the case.

According to this aspect, the end surface on the living body side of the second sealing member is pressed by the rear cover and the second sealing member is deformed. As a result, the pressing force of the second sealing member against the inner circumferential surface of the outer case increases, further increasing the sealing properties of the second sealing member and the inner circumferential surface of the outer case. Furthermore, because the intermediate portion of the end surface is formed in a protruding shape, even in a case where the second sealing member is deformed, the second sealing member can be prevented from being caught between the outer case and the rear cover.

Advantageous Effects of Invention

The present invention can provide a blood pressure measurement device with a replaceable cuff and waterproof function.

BRIEF DESCRIPTION OF DRAWINGS

FIG. 1 is a perspective view illustrating a configuration of a blood pressure measurement device according to a first embodiment of the present invention.

FIG. 2 is an exploded perspective view illustrating the configuration of the blood pressure measurement device.

FIG. 3 is an exploded perspective view illustrating the configuration of the blood pressure measurement device.

FIG. 4 is a side view illustrating the configuration of the blood pressure measurement device.

FIG. 5 is an explanatory diagram illustrating a state in which the blood pressure measurement device is attached to the wrist.

FIG. 6 is a block diagram illustrating the configuration of the blood pressure measurement device.

Figure 7:
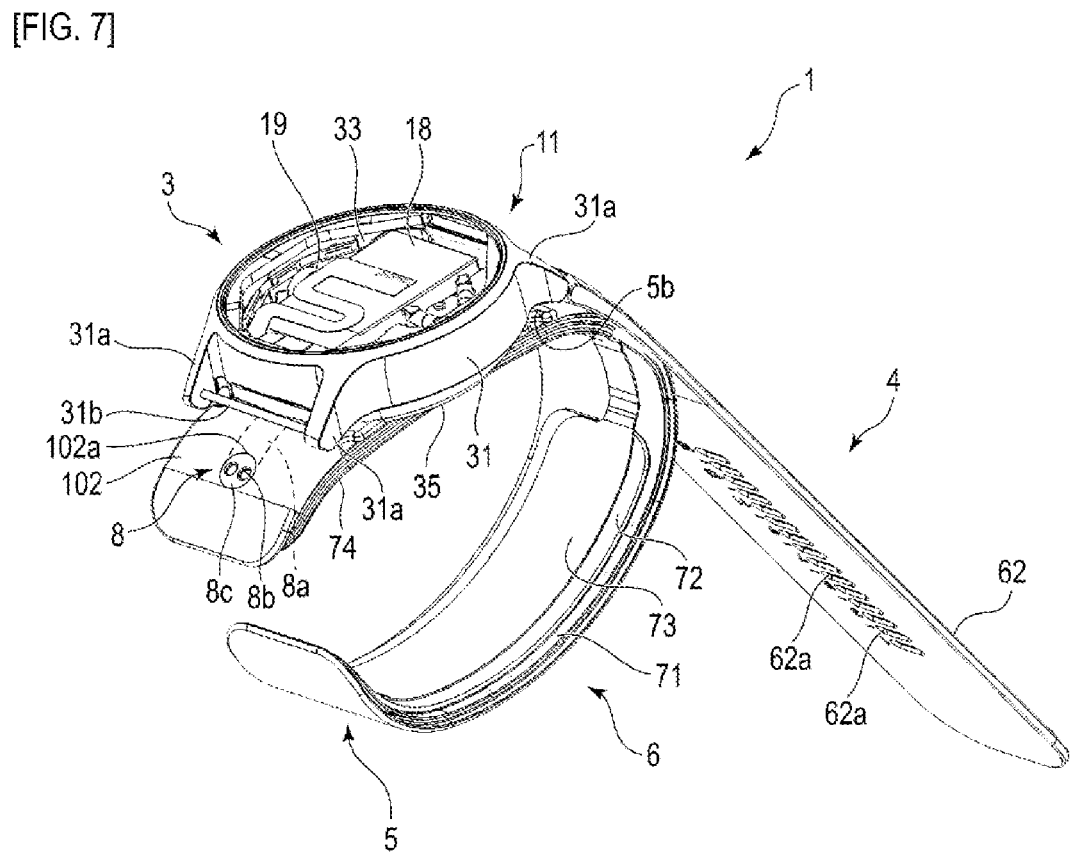

FIG. 7 is a perspective view illustrating the configuration of the blood pressure measurement device.

FIG. 8 is a perspective view illustrating the configuration of the blood pressure measurement device.

FIG. 9 is an exploded perspective view illustrating the configuration of the blood pressure measurement device.

FIG. 10 is an exploded perspective view illustrating the configuration of the blood pressure measurement device.

FIG. 11 is a perspective view illustrating the configuration of a base portion and a first seal of the blood pressure measurement device.

FIG. 12 is a cross-sectional view illustrating a configuration of the first seal and the surrounding region of the blood pressure measurement device.

FIG. 13 is a plan view illustrating the configuration of the first seal of the blood pressure measurement device.

FIG. 14 is an exploded perspective view illustrating the configuration of a curler and a cuff structure of the blood pressure measurement device.

FIG. 15 is a cross-sectional view illustrating the configuration of the curler and the cuff structure of the blood pressure measurement device.

FIG. 16 is a cross-sectional view illustrating the configuration of the curler and the cuff structure of the blood pressure measurement device.

FIG. 17 is a cross-sectional view illustrating the configuration of a tensile cuff of the blood pressure measurement device.

FIG. 18 is a cross-sectional view illustrating the configuration of a tensile cuff of the blood pressure measurement device.

FIG. 19 is a perspective view illustrating the configuration of the curler of the blood pressure measurement device.

FIG. 20 is a plan view illustrating the configuration of the cuff structure of the blood pressure measurement device.

FIG. 21 is a plan view illustrating the configuration of the cuff structure.

FIG. 22 is a plan view illustrating the configuration of a pressing cuff of the blood pressure measurement device.

FIG. 23 is a cross-sectional view illustrating the configuration of the pressing cuff.

FIG. 24 is a plan view illustrating the configuration of the sensing cuff of the blood pressure measurement device.

FIG. 25 is a cross-sectional view illustrating the configuration of the sensing cuff.

FIG. 26 is a flowchart illustrating an example of a method for manufacturing the blood pressure measurement device.

FIG. 27 is a flowchart illustrating an example of usage of the blood pressure measurement device.

FIG. 28 is a perspective view illustrating an example in which the blood pressure measurement device is attached to the wrist.

FIG. 29 is a perspective view illustrating an example in which the blood pressure measurement device is attached to the wrist.

FIG. 30 is a perspective view illustrating an example in which the blood pressure measurement device is attached to the wrist.

FIG. 31 is a cross-sectional view schematically illustrating a state in which the blood pressure measurement device is attached to a living body.

FIG. 32 is a cross-sectional view illustrating a configuration of the first seal and the surrounding region of the blood pressure measurement device according to a modified example.

DESCRIPTION OF EMBODIMENTS

An example of a blood pressure measurement device 1 according to a first embodiment of the present invention will be described below with reference to FIGS. 1 to 32.

FIG. 1 is a perspective view illustrating a configuration of the blood pressure measurement device 1 according to a first embodiment of the present invention. FIG. 2 is an exploded perspective view illustrating the configuration of the blood pressure measurement device 1. FIG. 3 is an exploded perspective view illustrating the configuration of the blood pressure measurement device 1 and is a perspective view of the blood pressure measurement device 1 from a different angle to that of FIG. 2.

FIG. 4 is a side view illustrating the configuration of the blood pressure measurement device 1. FIG. 5 is an explanatory diagram illustrating a state in which the blood pressure measurement device 1 is attached to the wrist 200. FIG. 6 is a block diagram illustrating the configuration of the blood pressure measurement device 1. FIG. 7 is a perspective view illustrating the configuration of the blood pressure measurement device 1 with some configurations removed. FIG. 8 is a perspective view illustrating the configuration of the blood pressure measurement device 1 with some configurations removed. FIG. 9 is an exploded perspective view illustrating the configuration of the blood pressure measurement device 1 with some configurations removed.

FIG. 10 is an exploded perspective view illustrating the configuration of the blood pressure measurement device 1 with some configurations removed. FIG. 11 is a perspective view illustrating the configuration of a base portion 33 and a first sealing member 36 of the blood pressure measurement device 1. FIG. 12 is a cross-sectional view illustrating a configuration of the first sealing member 36 and the surrounding region of the blood pressure measurement device 1. Specifically, FIG. 12 is a cross-sectional view illustrated as a line cross-section along XIII-XIII illustrated in FIG. 5.

FIG. 13 is a plan view illustrating the configuration of the first sealing member 36 of the blood pressure measurement device 1 as seen from a windshield 32 side.

FIG. 14 is an exploded perspective view illustrating the configuration of a curler 5 and a cuff structure 6 of the blood pressure measurement device 1. FIG. 15 is a cross-sectional view illustrating the configuration of the curler 5 and the cuff structure 6 of the blood pressure measurement device 1. FIG. 16 is a cross-sectional view illustrating the configuration of the curler 5 and the cuff structure 6 of the blood pressure measurement device 1. FIG. 17 is a cross-sectional view illustrating the configuration of a tensile cuff 74 of the blood pressure measurement device 1. FIG. 18 is a cross-sectional view illustrating the configuration of the tensile cuff 74 of the blood pressure measurement device 1. FIG. 19 is a perspective view illustrating the configuration of the curler 5 of the blood pressure measurement device 1. FIG. 20 is a plan view illustrating a configuration of the cuff structure 6 of the blood pressure measurement device 1 on the wrist 200 side. FIG. 21 is a plan view illustrating the configuration of the curler 5 of the cuff structure 6 on the inner circumferential surface side.

FIG. 22 is a plan view illustrating the configuration of a pressing cuff 71 of the blood pressure measurement device 1. FIG. 23 is a cross-sectional view illustrating the configuration of the pressing cuff 71, which is a line cross-section along XVIII-XVIII illustrated in FIG. 22. FIG. 24 is a plan view illustrating the configuration of a sensing cuff 73 of the blood pressure measurement device 1. FIG. 25 is a cross-sectional view illustrating the configuration of the sensing cuff 73 of the blood pressure measurement device 1, which is a line cross-section along XX-XX illustrated in FIG. 24.

FIG. 26 is a flowchart illustrating an example of a method for manufacturing the blood pressure measurement device 1. FIG. 27 is a flowchart illustrating an example of usage of the blood pressure measurement device 1. FIG. 28 is a perspective view illustrating an example in which the blood pressure measurement device 1 is attached to the wrist 200. FIG. 29 is a perspective view illustrating an example in which the blood pressure measurement device 1 is attached to the wrist 200. FIG. 30 is a perspective view illustrating an example in which the blood pressure measurement device 1 is attached to the wrist 200. FIG. 31 is a cross-sectional view schematically illustrating a state in which the blood pressure measurement device 1 is attached to the wrist 200. FIG. 32 is a cross-sectional view illustrating a configuration of the first sealing member 36 and the surrounding region of the blood pressure measurement device 1 according to a modified example.

The blood pressure measurement device 1 is an electronic blood pressure measurement device attached to a living body. The present embodiment will be described using an electronic blood pressure measurement device having an aspect of a wearable device attached to the wrist 200 of the living body.

As illustrated in FIGS. 1 to 9, the blood pressure measurement device 1 includes the device body 3, a belt 4 that fixes the device body 3 at the wrist, the curler disposed between the belt 4 and the wrist, the cuff structure 6 including the pressing cuff 71, the sensing cuff 73, and the tensile cuff 74, a fluid circuit 7 fluidly connecting the device body 3 and the cuff structure 6, and a power feeding unit 8 provided on the curler 5.

As illustrated in FIGS. 1 to 9, the device body 3 includes, for example, a case 11, a display unit 12, an operation unit 13, a pump 14, the flow path portion 15, the on-off valve 16, the pressure sensor 17, a power supply unit 18, a vibration motor 19, and a control substrate 20. The device body 3 supplies a fluid to the cuff structure 6 using the pump 14, the on-off valve 16, the pressure sensor 17, the control substrate 20, and the like.

As illustrated in FIGS. 1 to 4, the case 11 includes an outer case 31, the windshield 32 covering an opening of the outer case 31 on the opposite side (outer side) to the wrist 200, the base portion 33 provided inside the outer case 31 on the wrist 200 side, the rear cover 35 covering the wrist 200 side of the outer case 31, the first sealing member 36 provided on the lower surface of the rear cover 35, and a second sealing member 37 provided on the base portion 33.

The outer case 31 is formed in a cylindrical shape. The outer case 31 includes pairs of lugs 31*a* provided at respective symmetrical positions in the circumferential direction of an outer circumferential surface, and spring rods 31*b* each provided between each of the two pairs of lugs 31*a*. In addition, as illustrated in FIG. 9, for example, the outer case 31 includes screw holes 31*c* at four sections on the surface (rear surface) on the wrist 200 side that are at the roots of the pairs of lugs 31*a* respectively provided at symmetrical positions in the circumferential direction of the outer circumferential surface. The windshield 32 is, for example, a circular glass plate.

Specifically, the outer case 31 is configured to have a flat plate-like shape between the first pair of lugs 31*a* and between the second pair of lugs 31*a*, and is configured to have a plate-like shape with an arcuate curve in the portions between the first pair of lugs 31*a* and the second pair of lugs 31*a*.

Also, as illustrated in FIG. 8, in the outer case 31, a hole 31*g* is formed between the first pair of lugs 31*a* and between the second pair of lugs 31*a*. The holes 31*g* communicate from the inside of the outer case 31 to the outside. A filter is provided at an opening end of the hole 31*g* disposed on the inner circumferential surface of the outer case 31. The filter functions so as to allow air to pass through but to restrict the passage of water. Here, "restrict" refers to limiting the amount of water passed through. The filter is preferably capable of preventing the passage of water.

Also, as illustrated in FIG. 12, a sealing groove 31*e* is formed in the end portion on the wrist 200 side of an inner circumferential surface 31*d* of the outer case 31. The sealing groove 31*e* has a configuration in which a region of the sealing groove 31*e* from one end on the wrist 200 side of the inner circumferential surface 31*d* to an intermediate portion between the one end and the other end on the windshield 32 side in the axial direction D of the outer case 31 is formed to have a distance from a center line of the outer case 31 being longer than that of a region adjacent to this region on the windshield 32 side.

The sealing groove 31*e* is configured in a rectangular cross section, for example. An end surface 31*e*1 of the sealing groove 31*e* in the axial direction D of the outer case 31 is an abutting portion that restricts movement of the base portion 33 inside the outer case 31 by abutting against the base portion 33. The end surface 31*e*1 is constituted in a flat surface orthogonal to the axial direction D of the outer case 31, for example.

The base portion 33 holds the display unit 12, the operation unit 13, the pump 14, the on-off valve 16, the pressure sensor 17, the power supply unit 18, the vibration motor 19, and the control substrate 20. Additionally, the base portion 33 constitutes a portion of the flow path portion 15 that makes the pump 14 and the cuff structure 6 fluidly continuous. The base portion 33 is configured tin a planar shape that is substantially similar to the shape of the opening of the outer case 31.

As illustrated in FIG. 12, an outer circumference surface 33*a* of the base portion 33 is formed with a first protrusion portion 33*b* having an annular shape, which is disposed in the sealing groove 31*e* of the outer case 31 and protruding toward an inner circumferential surface 31*e*2 of the sealing groove 31*e*. At least a portion of an end surface 33*c* on the windshield 32 side of the first protrusion portion 33*b* is configured to abut on the end surface 31*e*1 of the sealing groove 31*e* of the outer case 31. For example, the outer edge portion of the end surface 33*c* abuts on the end surface 31*e*1. The end surface 33*c* is configured in a planar shape.

A second protrusion portion 33*d* having an annular shape protruding toward the inner circumferential surface 31*e*2 of the sealing groove 31*e* is formed on the outer circumferential surface of the first protrusion portion 33*b*. The second protrusion portion 33*d*, for example, is disposed on the outer circumferential surface of the first protrusion portion 33*b* at an intermediate portion between one end on the windshield 32 side and one end on the wrist 200 side. A cross section of the second protrusion portion 33*d* is configured in a rectangular shape, for example.

As illustrated in FIGS. 2 and 3, the rear cover 35 is configured as an annular shape with an open center. The rear cover 35 covers the end portion on the outer peripheral edge side of the outer case 31 on the wrist 200 side. With the rear cover 35 configured as such being integrally assembled with the curler 5, the central opening is covered by the curler 5, and the rear cover 35 together with the curler 5 forms a rear lid covering the end portion of the outer case 31 on the wrist 200 side. Specifically, the rear cover 35 is fixed to the curler 5 with four first joining members 35*a* and fixed to the end portion of the outer case 31 on the wrist 200 side with four second joining members 35*b*. The rear cover 35 includes four hole portions 35*c* into which the first joining members 35*a* that are provided at the bottom portion and fixed to the curler 5 are inserted, and four hole portions 35*d* provided at four portions of the outer circumferential portion that radially project out, into which the second joining members 35*b* that are fixed to the outer case 31 are inserted. A surface of the rear cover that abuts on the curler 5 is configured in a planar shape.

Also, as illustrated in FIG. 12, an edge portion 35*f* of the outer circumference of a surface 35*e* on the windshield 32 side of the rear cover 35 is configured to abut on an end surface 31*f* on the wrist 200 side of the outer case 31 and a surface on the wrist 200 side of the first protrusion portion 33*b* of the base portion 33.

In the present embodiment, the end surface 31*f* on the wrist 200 side of the outer case 31 and an end surface 33*e* on the wrist 200 side of the first protrusion portion 33*b* of the base portion 33 are disposed on the same plane in a state where the end surface 33*c* of the first protrusion portion 33*b* of the base portion 33 is abutting on the end surface 31*e*1 of the outer case 31. The edge portion 35*f* is configured in a planar shape.

The first joining members 35*a* and the second joining members 35*b* are members for mechanically fixing two components, such as a screw, a bolt, a machine screw, a rivet, or the like. In the present embodiment, the first joining members 35*a* and the second joining members 35*b* are screws.

As illustrated in FIGS. 2 and 9, the four first joining members 35*a* screw into the screw holes 5*e* provided at four sections of the cover portion 5*a*, described below, of the curler 5. The four second joining members 35*b* screw into the screw holes 31*c* provided at four sections in the outer case 31.

As illustrated in FIGS. 2 and 10, the four hole portions 35*c* are provided in the bottom surface of the rear cover 35 and provided at positions facing the cover portion 5*a*, described below, of the curler 5. For example, for the four hole portions 35*c*, the interval in the extension direction of the curler 5 is less than the interval in the direction orthogonal to the extension direction of the curler 5.

As illustrated in FIGS. 2 and 9, the four hole portions 35*d* are provided in projections facing four sections of the roots of the pairs of lugs 31*a* respectively provided at symmetrical positions in the circumferential direction of the outer circumferential surface and provided in the surface (rear surface) on the wrist 200 side of the outer case 31 on the outer circumferential portion of the rear cover 35. The four hole portions 35*d* face the screw holes 31*c* of the outer case 31 when the outer case 31 and the rear cover 35 are integrally combined.

As illustrated in FIGS. 2, 3, 8, and 10, the first sealing member 36 is a double-sided tape, for example, formed in the shape of the region of the rear cover 35 that comes into contact with the curler 5. The first sealing member 36 is configured in an annular shape disposed on the inner side of the opening of the rear cover 35. The first sealing member 36 seals between the curler 5 and the rear cover 35 by being provided between the abutting surfaces of the curler 5 and rear cover 35 abut each other.

As illustrated in FIGS. 2, 3, and 11 to 14, the second sealing member 37 is fixed to the outer circumferential surface of the first protrusion portion 33*b* of the base portion 33. The second sealing member 37 is configured in an annular shape. The second sealing member 37 is formed of a resin material. The second sealing member 37 is integrally formed with the base portion 33. The second sealing member 37 is formed by insert molding, for example. The second sealing member 37 seals between the inner circumferential surface 31*d* of the outer case 31 and the base portion 33 and between the rear cover 35 and the base portion 33.

Specifically, the second sealing member 37 is constituted such that, during a process in which the integral member of the base portion 33 and the second sealing member 37 is inserted in the outer case 31, the second sealing member 37 abuts on the inner circumferential surface 31*e*2 of the sealing groove 31*e*, is pressed to the center of the outer case 31, and deformed into a shape close contact with the inner circumferential surface 31*e*2. Furthermore, the second sealing member 37 is constituted in a shape such that it comes into close contact with the rear cover 35 in the axial direction D of the outer case 31. Furthermore, the second sealing member 37 is constituted such that, the second sealing member 37 is pressed in the axial direction D of the outer case 31 by the rear cover 35 and compressed between the outer case 31 and the rear cover 35, and thus the second sealing member 37 comes to have a shape close contact with the inner circumferential surface 31*d* of the outer case 31.

The second sealing member 37 is close contact with the inner circumferential surface of the outer case 31 and the rear cover 35 in this manner, and thus the second sealing member 37 has a higher sealing property than the first sealing member 36.

For the second sealing member 37, as illustrated in FIG. 12 by the two-dot dash line, in a state where the integral member of the base portion 33 and the second sealing member 37 is separated from the outer case 31, i.e., in a state before deformation, a distance L1 from the center of the outer case 31 in the direction orthogonal to the axial direction D of the outer case 31 to the outermost edge of the second sealing member 37 is longer than a distance L2 from the center of the outer case 31 in the direction orthogonal to the axial direction D of the outer case 31 to the inner circumferential surface 31*e*2 of the sealing groove 31*e* of the outer case 31.

Also, as illustrated by the two-dot dash line, an intermediate portion 37*b* between the end of the windshield 32 side and the end on the rear cover 35 side of an outer circumferential surface 37*a* of the second sealing member 37 in a state before deformation corresponds to the outermost edge protruding the furthest out in the direction orthogonal to the axial direction D of the outer case 31. Also, a region 37*c* from the end on the windshield 32 side of the outer circumferential surface 37*a* to the intermediate portion 37*b* is constituted as a surface that progressively expands in diameter from the end to the intermediate portion 37*b*. Furthermore, in a state before the second sealing member 37 is housed inside the outer case 31, the end on the windshield 32 side of the outer circumferential surface 37*a* is constituted in a smaller diameter than the opening end on the wrist 200 side of the sealing groove 31*e*.

An end surface 37*d* on the windshield 32 side of the second sealing member 37 is constituted on the same plane as the end surface 33*c* of the first protrusion portion 33*b*. In addition, in a state before the rear cover 35 is fixed to the outer case 31, an intermediate portion of the second sealing member 37 in the radial direction of an end surface 37*e* on the rear cover 35 side is configured as a protrusion protruding further to the rear cover 35 side than the end surface 33*c* on the rear cover 35 side of the first protrusion portion 33*b* of the base portion 33 and the end surface 31*f* on the wrist 200 side of the outer case 31. The end surface 37*e* is constituted in a shape that progressively narrows in width toward to the rear cover 35 side, for example.

The display unit 12 is disposed on the base portion 33 of the outer case 31 and directly below the windshield 32. As illustrated in FIG. 6, the display unit 12 is electrically connected to the control substrate 20. The display unit 12 is, for example, a liquid crystal display or an organic electroluminescence display. The display unit 12 displays various types of information including the date and time and measurement results of blood pressure values such as the systolic blood pressure and diastolic blood pressure, heart rate, and the like.

The operation unit 13 is configured to be capable of receiving an instruction input from a user. For example, the operation unit 13 includes a plurality of buttons 41 provided on the case 11, a sensor 42 that detects operation of the buttons 41, and a touch panel 43 provided on the display unit 12 or the windshield 32, as illustrated in FIGS. 1 and 6. When operated by the user, the operation unit 13 converts an instruction into an electrical signal. The sensor 42 and the touch panel 43 are electrically connected to the control substrate 20 to output electrical signals to the control substrate 20.

As the plurality of buttons 41, for example, three buttons are provided. The buttons 41 are supported by the base portion 33 and protrude from the outer circumferential surface of the outer case 31. The plurality of buttons 41 and a plurality of the sensors 42 are supported by the base portion 33. The touch panel 43 is integrally provided on the windshield 32, for example.

The pump 14 is, for example, a piezoelectric pump. The pump 14 compresses air and supplies compressed air to the cuff structure 6 through the flow path portion 15. The pump 14 is electrically connected to the control substrate 20.

The flow path portion 15 constitutes the flow path connecting from the pump 14 to the pressing cuff 71 and the tensile cuff 74 and a flow path connecting from the pump 14 to the sensing cuff 73, as illustrated in FIG. 6. Additionally, the flow path unit 15 constitutes a flow path connecting from the pressing cuff 71 and the tensile cuff 74 to the atmosphere, and a flow path connecting from the sensing cuff 73 to the atmosphere. The flow path unit 15 is a flow path of air constituted by a hollow portion, a groove, a flow path tank, a tube, or the like provided in the base portion 33 and the like.

The on-off valve 16 opens and closes a portion of the flow path portion 15. Specifically, a plurality of on-off valves 16, specifically four on-off valves 16 are provided, for example, as illustrated in FIG. 6, and selectively open and close the flow path connecting from the pump 14 to the pressing cuff 71 and the tensile cuff 74, the flow path connecting from the pump 14 to the sensing cuff 73, the flow path connecting from the pressing cuff 71 and the tensile cuff 74 to the atmosphere, and the flow path connecting from the sensing cuff 73 to the atmosphere, by the combination of opening and closing of each of the on-off valves 16. As a specific example, the four on-off valves 16 are constituted by the first on-off valve 16A, the second on-off valve 16B, the third on-off valve 16C, and the fourth on-off valve 16D. The first on-off valve 16A opens and closes the flow path connecting the pump 14 and the sensing cuff 73. The second on-off valve 16B opens and closes the flow path connecting the pump 14 and the tensile cuff 74. The second on-off valve 16B and the third on-off valve 16C open and close the flow path connecting the pump 14 and the pressing cuff 71. The second on-off valve 16B, the third on-off valve 16C, and the fourth on-off valve 16D open and close the flow path connecting the pump 14 and the atmosphere.

The pressure sensor 17 at least detects the pressure of the sensing cuff 73. The pressure sensor 17 is provided with the first pressure sensor 17A and the second pressure sensor 17B, for example. The pressure sensor 17 converts a detected pressure into an electrical signal, and outputs the electrical signal to the control substrate 20. For example, the first pressure sensor 17A and the second pressure sensor 17B are provided in the flow path connecting the first pressure sensor 17A of the flow path portion 15 and the sensing cuff 73. The flow path is continuous through the pressing cuff 71, the sensing cuff 73, and the tensile cuff 74 to the pump 14 by the opening and closing of each of the on-off valves, and thus the pressure in these flow paths corresponds to the pressure in the internal space of the pressing cuff 71, the sensing cuff 73, and the tensile cuff 74 connecting to the pump 14.

Specifically, for example, the pressure sensor 17 detects the pressure of the sensing cuff 73, i.e., the pressure of the flow path portion 15 connecting the pump 14 and the sensing cuff 73, when the first on-off valve 16A is open and the second on-off valve 16B is closed. Also, the pressure sensor 17 detects the pressure of the sensing cuff 73 and the tensile cuff 74, i.e., the pressure of the flow path portion 15 connecting the pump 14, the sensing cuff 73, and the tensile cuff 74, when the first on-off valve 16A and the second on-off valve 16B are open and the third on-off valve 16C is closed. Furthermore, the pressure sensor 17 detects the pressure of the pressing cuff 71, the sensing cuff 73, and the tensile cuff 74, i.e., the pressure of the flow path portion 15 connecting the pump 14, the pressing cuff 71, the sensing cuff 73, and the tensile cuff 74, when the first on-off valve 16A, the second on-off valve 16B, and the third on-off valve 16C are open and the fourth on-off valve 16D is open or closed.

The power supply unit 18 is, for example, a secondary battery such as a lithium ion battery. The power supply unit 18 is electrically connected to the control substrate 20, as illustrated in FIG. 6. The power supply unit 18 supplies power to the control substrate 20.

As illustrated in FIG. 6, the control substrate 20 includes, for example, a substrate 51, an acceleration sensor 52, a communication unit 53, a storage unit 54, and a control unit 55. The control substrate 20 is constituted by the acceleration sensor 52, the communication unit 53, the storage unit 54, and the control unit 55 that are mounted on the substrate 51.

The substrate 51 is fixed to the base portion 33 of the case 11 using screws or the like.

The acceleration sensor 52 is, for example, a 3-axis acceleration sensor. The acceleration sensor 52 outputs, to the control unit 55, an acceleration signal representing acceleration of the device body 3 in three directions orthogonal to one another. For example, the acceleration sensor 52 is used to measure, from the detected acceleration, the amount of activity of a living body to which the blood pressure measurement device 1 is attached.

The communication unit 53 is configured to be capable to transmit and receive information to and from an external device wirelessly or by wire. For example, the communication unit 53 transmits information controlled by the control unit 55, and information of a measured blood pressure value, a pulse, and the like to an external device via a network, and receives a program or the like for software update from an external device via a network and sends the program or the like to the control unit 55.

In the present embodiment, the network is, for example, the Internet, but is not limited to this. The network may be a network such as a Local Area Network (LAN) provided in a hospital or may be direct communication with an external device using a cable or the like including a terminal of a predetermined standard such as a USB. Thus, the communication unit 53 may be configured to include a plurality of wireless antennas, micro-USB connectors, or the like.

The storage unit 54 pre-stores program data for controlling the overall blood pressure measurement device 1 and a fluid circuit 7, settings data for setting various functions of the blood pressure measurement device 1, calculation data for calculating a blood pressure value and a pulse from pressure measured by the pressure sensors 17, and the like. Additionally, the storage unit 54 stores information such as a measured blood pressure value and a measured pulse.

The control unit 55 is constituted by one or more CPUs, and controls operation of the overall blood pressure measurement device 1 and operation of the fluid circuit. The control unit 55 is electrically connected to and supplies power to the display unit 12, the operation unit 13, the pump 14, each of the on-off valves 16 and the pressure sensors 17. Additionally, the control unit 55 controls operation of the display unit 12, the pump 14, and the on-off valves 16, based on electrical signals output by the operation unit 13 and the pressure sensors 17.

For example, as illustrated in FIG. 6, the control unit 55 includes a main Central Processing Unit (CPU) 56 that controls operation of the overall blood pressure measurement device 1, and a sub-CPU 57 that controls operation of the fluid circuit 7.

For example, the main CPU 56 obtains measurement results such as blood pressure values, for example, the systolic blood pressure and the diastolic blood pressure, and the heart rate, from electrical signals output by the pressure sensor 17, and outputs an image signal corresponding to the measurement results to the display unit 12.

For example, the sub-CPU 57 drives the pump 14 and the on-off valves 16 to feed compressed air to the pressing cuff 71 and the sensing cuff 73 when an instruction to measure the blood pressure is input from the operation unit 13. In addition, the sub-CPU 57 controls driving and stopping of the pump 14 and opening and closing of the on-off valves 16 based on electrical signal output by the pressure sensors 17. The sub-CPU 57 controls the pump 14 and the on-off valves 16 to selectively feed compressed air to the pressing cuff 71 and the sensing cuff 73 and selectively depressurize the pressing cuff 71 and the sensing cuff 73.

As illustrated in FIGS. 1 to 5 and 9, the belt 4 includes a first belt 61 provided on the first pair of lugs 31*a* and the spring rod 31*b*, and a second belt 62 provided on the second pair of lugs 31*a* and the spring rod 31*b*. The belt 4 is wrapped around the wrist 200 with a curler 5 in between.

The first belt 61 is referred to as a so-called a parent and is configured like a band capable of being joined to the second belt 62. As illustrated in FIGS. 1 to 4, the first belt 61 includes a belt portion 61*a* and a buckle 61*b*. The belt portion 61*a* is configured like a band. The belt portion 61*a* is formed of an elastically deformable resin material. In addition, the belt portion 61*a* is flexible and includes a sheet-like insert member inside the belt portion 61*a* for suppressing stretching in the longitudinal direction of the belt portion 61*a*. The belt portion 61*a* includes a first hole portion 61*c* that is formed at one end portion and extends orthogonal to the longitudinal direction of the belt portion 61*a*, and a second hole portion 61*d* that is formed at the other end portion and extends orthogonal to the longitudinal direction of the first belt 61.

As illustrated in FIGS. 5 and 9, the first hole portion 61*c* is provided at the end portion of the belt portion 61*a* The first hole portion 61*c* has an inner diameter at which the spring rod 31*b* can be inserted into the first hole portion 61*c* and at which the first belt 61 can rotate with respect to the spring rod 31*b*. In other words, the first belt 61 is rotatably held by the outer case 31 by disposing the first hole portion 61*c* between the pair of lugs 31*a* and around the spring rod 31*b*.

As illustrated in FIGS. 1 and 4, the second hole portion 61*d* is provided at the leading end of the belt portion 61*a*. The buckle 61*b* is attached to the second hole portion 61*d*.

As illustrated in FIGS. 1 and 4, the buckle 61*b* includes a frame body 61*e* in a rectangular frame shape and a prong 61*f* rotatably attached to the frame body 61*e*. A side of the frame body 61*e* to which the prong 61*f* is attached is inserted into the second hole portion 61*d*, and the frame body 61*e* is mounted rotatably with respect to the belt portion 61*a*.

The second belt 62 is referred to as a so-called blade tip, and is configured in a band-like shape having a width at which the second belt 62 can be inserted into the frame body 61*e*. The second belt 62 is formed of an elastically deformable resin material. In addition, the second belt 62 is flexible and includes a sheet-like insert member inside the second belt 62 for suppressing stretching in the longitudinal direction of the second belt 62.

In addition, as illustrated in FIGS. 1 to 5 and 7, the second belt 62 includes a plurality of small holes 62*a* into which the prong 61*f* is inserted. Additionally, the second belt 62 includes a third hole portion 62*b* provided at first end portion of the second belt 62 and extending orthogonally to the longitudinal direction of the second belt 62. The third hole portion 62*b* has an inner diameter at which the spring rod 31*b* can be inserted into the third hole portion 62*b* and at which the second belt 62 can rotate with respect to the spring rod 31*b*. In other words, the second belt 62 is rotatably held by the outer case 31 by disposing the third hole portion 62*b* between the pair of lugs 31*a* and around the spring rod 31*b*.

The second belt 62 is inserted into the frame body 61*e*, and the prong 61*f* is inserted into the small hole 62*a*, and thus the first belt 61 and the second belt 62 are integrally connected together, and the belt 4 as described above, together with the outer case 31, comes to have an annular shape following along the circumferential direction of the wrist 200. By shaping the belt 4 in an annular shape following along the circumferential direction of the wrist 200, the curler 5 is pressed and elastically deformed to follow along the circumferential direction of the wrist of the wearer of the blood pressure measurement device 1.

As illustrated in FIGS. 1 to 5, the curler 5 is configured in a band-like shape that curves in such a manner as to follow along the circumferential direction of the wrist 200. The curler 5 is formed with a first end and a second end spaced apart from each other. For example, a first end side outer surface of the curler 5 is fixed to the rear cover 35 of the device body 3. The curler 5 is disposed at a position where the first end and the second end protrude more to one side of the wrist 200 than the rear cover 35. Accordingly, the curler 5 is disposed with the first end and the second end to one side of the wrist 200 when the blood pressure measurement device 1 is attached to the wrist 200. Furthermore, the first end and the second end of the curler 5 are located adjacent to each other at a predetermined distance from each other. The curler is formed of a resin material, for example. In a specific example, the curler 5 is formed of a polypropylene with a thickness of approximately 1 mm.

In a specific example, as illustrated in FIGS. 1 to 5, the curler 5 is configured in a band-like shape that curves in such a manner as to follow along the circumferential direction of the wrist. Furthermore, the curler 5 includes the disk-like cover portion 5*a* that is provided at a position facing the hand back side of the wrist 200 on the first end side, and constitutes the rear lid together with the rear cover 35, and an escape portion 5*b* that is provided in the peripheral region of the cover portion 5*a* and allows the second joining members 35*b* that fix the outer case 31 and the rear cover 35 to be moveable. For example, the cover portion 5*a* and the adjacent portion of the cover portion 5*a* of the curler 5 are formed in a plate-like shape, and the first and second end sides is formed curving with a predetermined curvature more than the cover portion 5*a*. Furthermore, the length of the curler 5 from the cover portion 5*a* to the first end is less than the length from the cover portion 5*a* to the second end. In a specific example, the shorter side of the curler 5 from the cover portion 5*a* to the first end is disposed on the hand back side of the wrist, and the longer side from the cover portion 5*a* to the second end extends from the hand back side of the wrist, passing through one side, to the hand palm-side of the wrist 200.

Additionally, as illustrated in FIGS. 4, 7, and 19, the curler 5 is formed in a shape with the second end located at the inner circumferential surface side of the first end side when the first end and the second end are brought close. In a specific example, the width of the curler 5 in the width direction of the wrist 200 is set to be greater on the hand back side of the wrist 200 than on the hand palm-side of the wrist 200.

Furthermore, the radius of curvature of the first end of the curler 5 on the hand back side of the wrist 200 is set to be greater than the radius of curvature of the second end on the hand palm-side of the wrist 200. According to such a configuration, when both end sides of the curler 5 are brought to abut, the second end is disposed further to the inward side of the curler 5 than the first end. Furthermore, the curler 5 is provided with a recess 5*c* provided adjacent to the cover portion 5*a* on a portion of the cover portion 5*a*, on the outer surface on the first end side from the cover portion 5*a*, and also on the outer surface on the shorter side extending from the cover portion 5*a*.

The cover portion 5*a* includes an insert member 5*d* for reinforcement which is inserted. The cover portion 5*a* is fixed to the wrist 200 side of the outer case 31 with the fixed rear cover 35 in between. The cover portion 5*a* includes screw holes 5*e* provided at positions facing the four hole portions 35*c* of the rear cover 35, into which the first joining members 35*a* for fixing the rear cover 35 are screwed, and includes three hole portions 5*f* for connecting the cuff structure 6 to the device body 3. The surface of the cover portion 5*a* that abuts on the rear cover 35 is set as a flat surface.

The escape portion 5*b* is a relief for disposing the second joining members 35*b* in the rear cover 35 and for disposing a tool for rotating the second joining members 35*b* in a manner so that the second joining members 35*b* do not interfere with the curler when the rear cover 35 is fixed to the outer case 31 from the rear cover 35 side with the second joining members 35*b*.

As illustrated in FIG. 19, the insert member 5*d* is a thin plate which is formed in the same shape as a shape of the main surface of the cover portion 5*a* or formed in a shape that is slightly smaller than a shape of the main surface of the cover portion 5*a*. The insert member 5*d* is formed of a material with a higher bending strength than the curler 5 such as a metal material. In a specific example, the insert member 5*d* is formed of a SUS material.

The three hole portions 5*f* include a first hole portion 5*f*1 formed with an inner diameter into which a connection portion 84 described below of the pressing cuff 71 can be inserted, a second hole portion 5*f*2 formed with an inner diameter into which a connection portion 93 described below of the sensing cuff 73 can be inserted, and the third hole portion 5/3 formed with an inner diameter into which a connection portion 103 described below of the tensile cuff 74 can be inserted. In the present embodiment, the second hole portion 5/2 is disposed in the cover portion 5a closer to the second end side on the hand palm-side of the curler 5 than the first hole portion 5/1 and the third hole portion 5/3.

The curler 5 with such a configuration is fixed to the outer case 31 with the first end and the second end orientated to face the second belt 62 of the belt 4. Also, the curler 5 at least at the position facing the hand palm-side of the wrist 200 curves along the circumferential direction along with the hand palm-side of the wrist 200, and thus the cuff structure 6 facing the hand palm-side of the wrist 200 is held in a curved state following along the shape of the hand palm-side of the wrist 200.

The curler 5 has a hardness appropriate to provide flexibility and shape retainability. Here, "flexibility" refers to deformation of the shape of the curler 5 in a radial direction at the time of application of an external force of the belt 4 to the curler 5. For example, "flexibility" refers to deformation of the shape of the curler 5 in a side view in which the curler 5 approaches the wrist, is along the shape of the wrist, or follows to the shape of the wrist when the curler 5 is pressed by the belt 4. Furthermore, "shape retainability" refers to the ability of the curler 5 to maintain a pre-imparted shape when no external force is applied to the curler 5. For example, "shape retainability" refers to, in the present embodiment, the ability of the curler 5 to maintain the shape in a shape curving along the circumferential direction of the wrist.

The cuff structure 6 is disposed on an inner circumferential surface of the curler 5, and is held along the shape of the inner circumferential surface of the curler 5. As a specific example, the cuff structure 6 is held by disposing the pressing cuff 71 and the tensile cuff 74 on the inner circumferential surface of the curler 5, and fixing the cuff structure 6 by a joining layer 75 provided between the curler 5 and the pressing cuff 71 and the tensile cuff 74. In the present embodiment, the joining layer 75 is adhesive or double-sided tape.

As illustrated in FIGS. 1 to 7 and 14 to 25, the cuff structure 6 includes the pressing cuff 71, a back plate 72, the sensing cuff 73, and the tensile cuff 74. Also, the cuff structure 6 is provided with the joining layer 75 for joining components each other and joining the curler 5 and the cuffs 71 and 74. The cuff structure 6 is fixed to the curler 5. The cuff structure 6 includes the pressing cuff 71, the back plate 72, and the sensing cuff 73 that are stacked one another and disposed on the curler 5, and the tensile cuff 74 that is spaced apart from the pressing cuff 71, the back plate 72, and the sensing cuff 73 and disposed on the curler 5.

In a specific example, as illustrated in FIG. 5, the cuff structure 6 is fixed to the inner circumferential surface of the curler 5 on the hand palm-side of the wrist 200 with the pressing cuff 71, the back plate 72, and the sensing cuff 73 stacked in this order from the inner circumferential surface of the curler 5 toward the wrist 200 side. In addition, the cuff structure 6 includes the tensile cuff 74 disposed on the inner circumferential surface of the curler 5 on the hand back side of the wrist 200. Each of the members of the cuff structure 6 is fixed to an adjacent member of the cuff structure 6 in a stacking direction by the joining layer 75.

The pressing cuff 71 is fluidly connected to the pump 14 through the flow path portion 15. The pressing cuff 71 is inflated to pressing the back plate 72 and the sensing cuff 73 toward the wrist 200 side. As illustrated in FIGS. 15, 16 and 20 to 23, the pressing cuff 71 includes a plurality of, for example, two-layer, air bags 81, a target join portion 82 provided on the air bag 81 facing the curler 5, a flow path body (first flow path body) 83 communicating with air bags 81, and the connection portion (first connection portion) 84 provided on the leading end of the flow path body 83. The pressing cuff 71 with such a configuration is configured by integrally welding a plurality of sheet members 86 together.

Here, the air bags 81 are bag-like structures (first bag-like structures), and in the present embodiment, the blood pressure measurement device 1 is configured to use air with the pump 14, and thus the present embodiment will be described using the air bags. However, in a case where a fluid other than air is used, the bag-like structures may be fluid bags that are inflated by a fluid. The plurality of air bags 81 are stacked and are in fluid communication with one another in the stacking direction.

Each of the air bags 81 is formed in a rectangular bag-like shape that is long in one direction. Additionally, the air bags 81 are set so that the width in the lateral direction is the same as the width in the lateral direction of the curler 5. The air bags 81 are each constituted by, for example, combining two sheet members 86 and, as illustrated in FIGS. 15, 16, and 20 to 23, welding a weld portion 81a using heat into a rectangular frame shape long in one direction. In addition, the two-layer air bags 81 are constituted by forming with integrally combining two air bags 81 by welding using heat, or with welding together a pair of sheet members 86 facing adjacent air bag 81 and welding to the air bag 81. In a specific example, the two-layer air bags 81 are fluidly continuous through openings provided in the sheet members 86 facing one another. In addition, in the two-layer air bags 81, by welding the opposing sheet members 86 together in a quadrilateral frame shape smaller than the weld portion 81a located on the outer peripheral edge and surrounding the plurality of openings with this weld portion (join portion) 81b, the adjacent air bags 81 are integrally formed and made to be fluidly continuous on the inner side of the weld portion 81b.

A single or a plurality of target join portions 82 are provided at at least a portion of the edge portion of the air bag 81 disposed adjacent to the curler 5. The target join portion 82 is formed by a portion of the sheet member 86 forming the air bag 81.

An example of the present embodiment will be described using the examples illustrated in FIGS. 15, 16, and 20 to 23 in which one target join portion 82 is provided on the edge portion in the lateral direction of each of the air bags 81. Note that, for example, the target join portion 82 may be divided in the longitudinal direction of the air bag 81 by a slit, or a plurality of target join portions 82 may be provided in the longitudinal direction of the air bag 81. The target join portion 82 is at least joined to the outer circumferential surface of the curler 5 when the pressing cuff 71 is disposed on the inner circumferential surface of the curler 5. Furthermore, for example, two target join portions 82 are stacked and welded.

Note that the two target join portions 82 are set to have a different length to the length in the lateral direction of the air bags 81, for example. In this example, the two target join portions 82 are stacked and welded at the first end side in the lateral direction of the curler 5. Note that as long as the two target join portions 82 are able to be disposed with the leading end on the outer circumferential surface of the curler 5, the length is able to be set as appropriate, and the two target join portions 82 may be stackable or not. However, in a case where the length is set to a stackable length, the length is preferably a length such that the leading end does not extend further out than the outer edge of the outer circumferential surface of the curler 5.

As illustrated in FIGS. 14 and 20 to 23, the flow path body 83 is integrally provided on a single air bag 81, for example, on a portion of one edge portion in the longitudinal direction of the air bag 81 adjacent to the curler 5. As a specific example, the flow path body 83 is provided at the end portion of the air bag 81 near the device body 3. Additionally, the flow path body 83 is formed in a shape that is long in one direction and has less width than the width of the air bag 81 in the lateral direction and formed with a leading end having a circular shape. The flow path body 83 includes the connection portion 84 on the leading end. The flow path body 83 is connected to the flow path portion 15 through the connection portion 84 and constitutes a flow path between the flow path portion 15 of the device body 3 and the air bag 81.

The flow path body 83 is constituted by welding a portion of sheet members 86, which is adjacent to a region of the sheet members 86 constituting the air bags 81, in a frame shape long in one direction using heat, in a state where the connection portion 84 is disposed on the two sheet members 86. The flow path body 83 with such a configuration is disposed between the inner circumferential surface of the curler 5 and the tensile cuff 74, and the leading end is disposed at a position facing the first hole portion **5*f*1 on the main surface on the wrist 200 side of the region where the cover portion 5*a* of the curler 5 is provided. In addition, the width of the flow path body 83 not including a weld portion 83*a*** is formed to be 3.8 mm, for example.

Note that, a portion of the weld portion **81*a*, where the two sheet members 86 are welded in a rectangular frame shape, is not welded and the air bags 81 provided with the flow path body 83 are constituted to be continuous with the weld portion 83*a* constituting the flow path body 83, and thus the air bags 81 are fluidly continuous with the flow path body 83**.

The connection portion 84 is, for example, a nipple. The connection portion 84 is provided at the leading end of the flow path body 83. The leading end of the connection portion 84 is exposed from the sheet member 86, facing the curler 5, of the two sheet members 86 constituting the flow path body 83. The connection portion 84 is inserted in the first hole portion **5*f*1 of the cover portion 5*a* and is connected to the flow path portion 15**.

As a specific example, as illustrated in FIGS. 15, 16, and 31, the pressing cuff 71 includes a first sheet member **86*a*, a second sheet member 86*b*, a third sheet member 86*c*, and a fourth sheet member 86*d* in this order from the wrist 200 side. The second sheet member 86*b* constitutes a first-layer air bag 81 along with the first sheet member 86*a*, the third sheet member 86*c* is integrally joined to the second sheet member 86*b* and constitutes the target join portion 82, and the fourth sheet member 86*d* constitutes a second-layer air bag 81 and the flow path body 83 along with the third sheet member 86*c*. Note that the pressing cuff 71 is integrally constituted by joining adjacent sheet members 86** by welding using heat.

The first sheet member **86*a* and the second sheet member 86*b* are configured in a similar rectangular shape to the air bags 81, and peripheral edge portions of the four sides are welded to constitute the air bags 81. The second sheet member 86*b* and the third sheet member 86*c* are disposed facing each other, and each includes a plurality of openings 86*b*1 and 86*cl* through which the two air bags 81 are fluidly continuous. Additionally, the second sheet member 86*b* and the third sheet member 86*c* are integrally joined by the peripheral region of the plurality of openings 86*b*1 and 86*cl* being welded using heat in a quadrilateral frame shape smaller than the welded four sides of the air bags 81**.

The third sheet member **86*c*, for example, is constituted in a shape that allows the air bags 81, the target join portion 82, and the flow path body 83 to be constituted. The fourth sheet member 86*d*, for example, is constituted in a shape that allows the air bags 81 and the flow path body 83 to be constituted. Furthermore, the fourth sheet member 86*d* includes a hole portion 86*d*1 into which the leading end of the connection portion 84** can be inserted, for example.

The air bags 81, the target join portion 82, and the flow path body 83 are constituted by the third sheet member **86*c* and the fourth sheet member 86*d* being disposed facing one another, welded using heat along the peripheral edge shape of the air bag 81 and the flow path body 83 so that the air bag 81 and the flow path body 83** are fluidly continuous, and cut in a predetermined shape.

The hole portion **86*d*1 of the fourth sheet member 86*d* is disposed with the connection portion 84, and the peripheral region of the hole portion 86*d*1 is welded to the connection portion 84 using heat. Furthermore, the fourth sheet member 86*d* is joined with the inner circumferential surface of the curler 5 with the joining layer 75 in between, and the target join portion 82 of the third sheet member 86*c* is joined to the outer circumferential surface of the curler 5 with the joining layer 75** in between.

As illustrated in FIGS. 15, 16, and 31, the back plate 72 is applied to the outer surface of the first sheet member **86*a* of the pressing cuff 71 by the joining layer 75. The back plate 72 is formed in a plate shape using a resin material. The back plate 72 is made of polypropylene, for example, and is formed into a plate shape having a thickness of approximately 1 mm. The back plate 72** has shape followability.

Here, “shape followability” refers to a function of the backplate 72 by which the back plate 72 can be deformed in such a manner as to follow the shape of a contacted portion of the wrist 200 to be disposed, the contacted portion of the wrist 200 refers to a region of the wrist 200 that is faced by the back plate 72. Here, the contact as used herein includes both direct contact and indirect contact with the sensing cuff 73 in between.

For example, as illustrated in FIG. 16, the back plate 72 includes a plurality of grooves **72*a* extending in both main surfaces of the back plate 72 in a direction orthogonal to the longitudinal direction. The plurality of grooves 72*a* face the corresponding grooves 72*a* provided in the other main surface in the thickness direction of the back plate 72. Additionally, the plurality of grooves 72*a* are disposed at equal intervals in the longitudinal direction of the back plate 72**.

In the back plate 72, portions including the plurality of grooves **72*a* are thinner than portions including no grooves 72*a* and thus the portions including the plurality of grooves 72*a* are easily deformed. Accordingly, the back plate 72 is deformed in such a manner as to follow to the shape of the wrist 200, and has shape followability of extending in the circumferential direction of the wrist. The back plate 72 is formed such that the length of the back plate 72 is sufficient to cover the hand palm-side of the wrist 200. The back plate 72 transfers the pressing force from the pressing cuff 71 to the back plate 72 side main surface of the sensing cuff 73 in a state in which the back plate 72 is extending along the shape of the wrist 200**.

The sensing cuff 73 is fluidly connected to the pump 14 through the flow path portion 15. The sensing cuff 73 is fixed to the main surface of the back plate 72 on the wrist 200 side. The sensing cuff 73 is in direct contact with a region of the wrist 200 where an artery 210 resides, as illustrated in FIGS. 5 and 31. The artery 210 as used herein is the radial artery and the ulnar artery. The sensing cuff 73 is formed in the same shape as that of the back plate 72 or a shape that is smaller than that of the back plate 72, in the longitudinal direction and the width direction of the back plate 72. The sensing cuff 73 is inflated to compress a hand palm-side region of the wrist 200 in which the artery 210 resides. The sensing cuff 73 is pressed by the inflated pressing cuff 71 toward the wrist 200 side with the back plate 72 in between.

In a specific example, as illustrated in FIGS. 15, 16, and 24 to 25, the sensing cuff 73 includes one air bag 91, a flow path body (second flow path body) 92 that communicates with the air bag 91, and the connection portion 93 provided at the leading end of the flow path body 92. One main surface of the air bag 91 of the sensing cuff 73 is fixed to the back plate 72. For example, the sensing cuff 73 is joined to the main surface of the back plate 72 on the wrist 200 side by the joining layer 75. The sensing cuff 73 with such a configuration is constituted by welding two sheet members 96.

Here, the air bags 91 are bag-like structures (second bag-like structures), and in the present embodiment, the blood pressure measurement device 1 is configured to use air with the pump 14, and thus the present embodiment will be described using the air bags. However, in a case where a fluid other than air is used, the bag-like structures may be fluid bags that are inflated by a fluid.

The air bag 91 is constituted in a rectangular shape that is long in one direction. The air bags 91 are each constituted by, for example, combining two sheet members 96 long in one direction and, as illustrated in FIGS. 15, 16, and 24 to 25, welding a weld portion 91*a* using heat into a rectangular frame shape long in one direction. Also, the air bag 91, for example, includes a junction margin 91*b* for ensuring area for joining the air bag 91 to the back plate 72 using the joining layer 75. The junction margin 91*b* is formed by the sheet member 96 facing the back plate 72, for example.

The flow path body 92 is integrally provided at a portion of one edge portion of the air bag 91 in the longitudinal direction. As a specific example, the flow path body 92 is provided at the end portion of the air bag 91 near the device body 3. Additionally, the flow path body 92 is formed in a shape that is long in one direction and has less width than the width of the air bag 91 in the lateral direction, and formed with a leading end having a circular shape. The flow path body 92 includes the connection portion 93 on the leading end. The flow path body 92 is connected to the flow path portion 15 through the connection portion 93 and constitutes a flow path between the flow path portion 15 of the device body 3 and the air bag 91.

The flow path body 92 is constituted by welding a portion of sheet members 96, which is adjacent to a region of the sheet members 96 constituting the air bag 91, in a frame shape long in one direction using heat, in a state where the connection portion 93 is disposed on the two sheet members 96. Note that, a portion of the weld portion 91*a*, where the two sheet members 96 are welded in a rectangular frame shape, is not welded and the air bag 91 is constituted to be continuous with the weld portion 92*a* constituting the flow path body 92, and thus the air bag 91 and the flow path body 92 are fluidly continuous. The flow path body 92 with such a configuration is disposed between the inner circumferential surface of the curler 5 and the tensile cuff 74, and the leading end is disposed at a position facing the second hole portion 5*f*2 on the main surface on the wrist 200 side of the region where the cover portion 5*a* of the curler 5 is provided. In addition, the width of the flow path body 92 not including the weld portion 92*a* is 3.8 mm, for example.

The connection portion 93 is, for example, a nipple. The connection portion 93 is provided at the leading end of the flow path body 92. Also, the leading end of the connection portion 93 is externally exposed from the sheet member 96 facing the curler and the back plate 72, of the two sheet members 96 constituting the flow path body 92. The connection portion 93 is inserted in the second hole portion 5*f*2 of the cover portion 5*a* and is connected to the flow path portion 15.

In a specific example, the sensing cuff 73 includes a fifth sheet member 96*a* and a sixth sheet member 96*b* in this order from the wrist 200 side as illustrated in FIGS. 15 and 16. Note that the sensing cuff 73 is constituted by joining adjacent sheet members 96 by welding using heat.

For example, the fifth sheet member 96*a* and the sixth sheet member 96*b* are constituted in a shape that allows the air bag 91, the junction margin 91*b*, and the flow path body 92 to be constituted. The air bag 91 and the flow path body 92 are constituted by the fifth sheet member 96*a* and the sixth sheet member 96*b* being disposed facing one another, welded using heat along the peripheral edge shape of the air bag 91 and the flow path body 92 so that the air bag 91 and the flow path body 92 are fluidly continuous, and cut in a predetermined shape.

Furthermore, the sixth sheet member 96*b* includes a hole portion 96*b*1 into which the leading end of the connection portion 93 can be inserted, for example. The connection portion 93 is disposed in the hole portion 96*b*1, and the peripheral region of the hole portion 96*b*1 is welded to the connection portion 93 using heat. The sixth sheet member 96*b* is joined to the inner circumferential surface of the back plate 72 with the joining layer 75 in between.

The tensile cuff 74 is fluidly connected to the pump 14 through the flow path portion 15. The tensile cuff 74 is inflated to press the curler 5 such that the curler 5 is spaced apart from the wrist 200, pulling the belt 4 and the curler 5 toward the hand back side of the wrist 200. As illustrated in FIGS. 17 and 18, the tensile cuff 74 includes a plurality of, for example, six-layer air bags 101, a target join portion 102 provided on the air bag 101 facing the curler 5, and the connection portion (third connection portion) 103 provided on the air bag 101 facing the curler 5. The tensile cuff 74 with such a configuration is constituted by welding a plurality of sheet members 106. In addition, the tensile cuff 74 is fixed to the region where the flow path bodies 83 and 92 are provided and the curler 5, including the cover portion 5*a*, on the hand back side of the wrist 200. In other words, the flow path body 83 of the pressing cuff 71 and the flow path body 92 of the sensing cuff 73 are disposed between the curler 5 on the hand back side of the wrist 200 and the tensile cuff 74.

Additionally, the tensile cuff 74 is configured such that the thickness of the tensile cuff 74 in an inflating direction, in the present embodiment, in the direction in which the curler 5 and the wrist 200 face each other, during inflation, is larger than the thickness of the pressing cuff 71 in the inflating direction during inflation and than the thickness of the sensing cuff 73 in the inflating direction during inflation. Specifically, the air bags 101 of the tensile cuff 74 include more layer structures than the air bags 81 in the pressing cuff 71 and the air bag 91 in the sensing cuff 73, and have thicker thickness than the pressing cuff 71 and the sensing cuff 73 when the air bags 101 are inflated from the curler 5 toward the wrist 200.

Here, the air bags 101 are bag-like structures (third bag-like structures), and in the present embodiment, the blood pressure measurement device 1 is configured to use air with the pump 14, and thus the present embodiment will be described using the air bags. However, in a case where a fluid other than air is used, the bag-like structures may be fluid bags that are inflated by a fluid. A plurality of the air bags 101 are stacked and are in fluid communication in the stacking direction.

Each of the air bags 101 is formed in a rectangular bag-like shape that is long in one direction. Additionally, the air bags 101 are set so that the width in the lateral direction is the same as the width in the lateral direction of the curler 5. The air bags 101 are each constituted by, for example, combining two sheet members 106 and, as illustrated in FIGS. 17, 18, 20, and 21, welding a weld portion 101*a* using heat into a rectangular frame shape long in one direction. In addition, the six-layer air bags 101 are, for example, constituted by forming with integrally combining six air bags 101 by welding using heat, or with welding together a pair of sheet members 106 facing adjacent air bag 101 and welding to the air bag 101. The six-layer air bags 101 are fluidly continuous through openings provided in the sheet members 106 facing one another. In addition, in the six-layer air bags 101, by welding the opposing sheet members 106 together in a quadrilateral frame shape smaller than the weld portion 81*a* located on the outer peripheral edge and surrounding the plurality of openings with a weld portion (join portion) 101*b*, the adjacent air bags 101 are integrally formed and made to be fluidly continuous on the inner side of the weld portion 101*b*.

A single or a plurality of target join portions 102 are provided at at least a portion of the edge portion of the air bag 101 disposed adjacent to the curler 5. The target join portion 102 is formed by a portion of the sheet member 106 forming the air bag 101.

An example of the present embodiment will be described using examples in which two target join portions 102 are each provided in the longitudinal direction of the air bags 101 on the edge portion in the lateral direction of each of the air bags 101. Note that, for example, the target join portions 102 are provided on the air bags 101 avoiding the positions facing the cover portion 5*a* of the curler 5. Furthermore, for example, the target join portion 102 includes an escape portion 102*a*, which is for externally exposing a power feeding terminal 8*b* described below of the power feeding unit 8 provided on the curler 5, at a portion facing the power feeding terminal 8*b*. The escape portion 102*a*, for example, is an opening through which the power feeding terminal 8*b* can be externally exposed and has a circular shape as an example.

The target join portion 102 is at least joined to the outer circumferential surface of the curler 5 when the tensile cuff 74 is disposed on the inner circumferential surface of the curler 5. Additionally, the target join portions 102 disposed at the same position in the lateral direction of the air bags 101 are stacked and welded.

Note that the two target join portions 102 are set to have a different length to the length in the lateral direction of the air bags 101, for example. In this example, the two target join portions 102 are stacked and welded at the first end side in the lateral direction of the curler 5. Note that as long as the two target join portions 102 are able to be disposed with the leading end on the outer circumferential surface of the curler 5, the length is able to be set as appropriate and the two target join portions 102 may be stackable or not. However, in a case where the length is set to a stackable length, the length is preferably a length such that the leading end does not extend further out than the outer edge of the outer circumferential surface of the curler 5.

The connection portion 103 is, for example, a nipple. The connection portion 103 is provided at a position facing the third hole portion **5*f*3 of the cover portion 5***a* in a central region in the longitudinal direction of the air bag 101 disposed adjacent to the curler 5. The leading end of the connection portion 103 is exposed from the sheet member 106 facing the curler 5, of the two sheet members 106 forming the air bag 101. The connection portion 103 is inserted in the third hole portion **5*f*3 of the cover portion 5***a* and is connected to the flow path portion 15.

In a specific example, as illustrated in FIGS. 17 and 18, the tensile cuff 74 includes a seventh sheet member 106*a*, an eighth sheet member 106*b*, a ninth sheet member 106*c*, a tenth sheet member 106*d*, an eleventh sheet member 106*e*, a twelfth sheet member 106*f*, a thirteenth sheet member 106*g*, a fourteenth sheet member 106*h*, a fifteenth sheet member 106*i*, a sixteenth sheet member 106*j*, a seventeenth sheet member 106*k*, and an eighteenth sheet member 106*l* in this order from the wrist 200 side. Note that the tensile cuff 74 is integrally constituted by joining adjacent sheet members 106 by welding using heat.

The seventh sheet member 106*a* to the eighteenth sheet member 106*l* are constituted in a similar rectangular shape to the air bags 101. Edge portions of four sides of the seventh sheet member 106*a* are welded to corresponding peripheral edge portions of four sides of the eighth sheet member 106*b* to constitute a first-layer air bag 101. The eighth sheet member 106*b* and the ninth sheet member 106*c* are disposed facing each other, and each includes a plurality of openings **106*b*1 and 106*cl* through which the two air bags 101 are fluidly continuous. Additionally, the eighth sheet member 106***b* and the ninth sheet member 106*c* are integrally joined by the peripheral region of the plurality of openings **106*b*1 and 106*cl* being welded using heat in a quadrilateral frame shape smaller than the welded four sides of the air bags 101**.

Edge portions of four sides of the ninth sheet member 106*c* are welded to corresponding peripheral edge portions of four sides of the tenth sheet member 106*d* to constitute a second-layer air bag 101.

As illustrated in FIGS. 17 and 18, the tenth sheet member 106*d* and the eleventh sheet member 106*e* include a plurality of openings **106*d*1 and 106*e*1 disposed facing one another and through which the two air bags 101 are fluidly continuous. Additionally, the tenth sheet member 106***d* and the eleventh sheet member 106*e* are integrally joined by the peripheral region of the plurality of openings **106*d*1 and 106*e*1 being welded using heat in a quadrilateral frame shape smaller than the welded four sides of the air bags 101. Edge portions of four sides of the eleventh sheet member 106***e* are welded to corresponding peripheral edge portions of four sides of the twelfth sheet member 106*f* to constitute a third-layer air bag 101.

As illustrated in FIGS. 17 and 18, the twelfth sheet member 106*f* and the thirteenth sheet member 106*g* include a plurality of openings **106*f*1 and 106*g*1 disposed facing one another and through which the two air bags 101 are fluidly continuous. Additionally, the twelfth sheet member 106***f* and the thirteenth sheet member 106*g* are integrally joined by the peripheral region of the plurality of openings **106*f*1 and 106*g*1 being welded using heat in a quadrilateral frame shape smaller than the welded four sides of the air bags 101**.

Edge portions of four sides of the thirteenth sheet member 106*g* are welded to corresponding peripheral edge portions of four sides of the fourteenth sheet member 106*h* to constitute a fourth-layer air bag 101.

As illustrated in FIGS. 17 and 18, the fourteenth sheet member 106*h* and the fifteenth sheet member 106*i* include a plurality of openings 106*h*1 and 106*i*1 disposed facing one another and through which the two air bags 101 are fluidly continuous. Additionally, the fourteenth sheet member 106*h* and the fifteenth sheet member 106*i* are integrally joined by the peripheral region of the plurality of openings 106*h*1 and 10611 being welded using heat in a quadrilateral frame shape smaller than the welded four sides of the air bags 101. Edge portions of four sides of the fifteenth sheet member 106*i* are welded to corresponding peripheral edge portions of four sides of the sixteenth sheet member 106*j* to constitute a fifth-layer air bag 101.

As illustrated in FIGS. 17 and 18, the sixteenth sheet member 106*j* and the seventeenth sheet member 106*k* include a plurality of openings 106*j*1 and 106*kl* disposed facing one another and through which the two air bags 101 are fluidly continuous. Also, the seventeenth sheet member 106*k*, for example, is constituted in a shape that allows the air bag 101 and the target join portion 102 to be constituted. Additionally, the sixteenth sheet member 106*j* and the seventeenth sheet member 106*k* are integrally joined by the peripheral region of the plurality of openings 106*j*1 and 106*kl* being welded using heat in a quadrilateral frame shape smaller than the welded four sides of the air bags 101. The seventeenth sheet member 106*k* and the eighteenth sheet member 106*l* are welded using heat along the peripheral edge shape of the air bag 101 and cut in a predetermined shape to constitute a sixth-layer air bag 101 and the target join portion 102.

Furthermore, the eighteenth sheet member 106*l* includes a hole portion 10611 into which the leading end of the connection portion 103 can be inserted, for example. The eighteenth sheet member 106*l* is disposed with the connection portion 103 at the hole portion 10611, and the peripheral region of the hole portion 10611 is welded to the connection portion 103 using heat. Furthermore, the eighteenth sheet member 106*l* is joined with the inner circumferential surface of the curler 5 with the joining layer 75 in between, and the target join portion 102 of the seventeenth sheet member 106*k* is joined to the outer circumferential surface of the curler 5 with the joining layer 75 in between.

Additionally, each of the sheet members 86, 96, and 106 forming the pressing cuff 71, the sensing cuff 73, and the tensile cuff 74 are formed of a thermoplastic resin material. The thermoplastic resin material is a thermoplastic elastomer. Examples of thermoplastic resin material constituting the sheet members 86, 96, and 106 include thermoplastic polyurethane based resin (hereinafter referred to as TPU), polyvinyl chloride resin, ethylene-vinyl acetate resin, thermoplastic polystyrene based resin, thermoplastic polyolefin resin, thermoplastic polyester based resin, and thermoplastic polyamide resin. Note that, in the pressing cuff 71 and the sensing cuff 73, of at least the plurality of sheet members 86 and 106 constituting the air bags 81 and 101, at least the sheet members 86 and 106 welded to the curler 5 are constituted by a material similar to the material of the curler 5.

For example, the sheet members 86, 96, and 106 are formed using a molding method such as T-die extrusion molding or injection molding. After being molded by each molding method, the sheet members 86, 96, and 106 are sized into predetermined shapes, and the sized individual pieces are joined by welding or the like to constitute bag-like structures 81, 91, and 101. A high frequency welder or laser welding is used as the welding method.

The fluid circuit 7 is constituted by the case 11, the pump 14, the flow path portion 15, the on-off valves 16, the pressure sensors 17, the pressing cuff 71, the sensing cuff 73, and the tensile cuff 74. A specific example of the fluid circuit 7 will be described below.

As illustrated in FIG. 6, for example, the fluid circuit 7 includes a first flow path 7*a* in which the pump 14, the sensing cuff 73, the first pressure sensor 17A and the second pressure sensor 17B are continuous through the first on-off valve 16A, a second flow path 7*b* which is constituted by branching from the first flow path 7*a* between the pump 14 and the first on-off valve 16A and is continuous from the pump 14 to the atmosphere through the second on-off valve 16B, the third on-off valve 16C, and the fourth on-off valve 16D in this order, a third flow path 7*c* which is constituted by branching from an intermediate portion of the second flow path 7*b* between the second on-off valve 16B and the third on-off valve 16C and is continuous from the pump 14 to the tensile cuff 74, and a fourth flow path 7*d* which is constituted by branching from an intermediate portion of the second flow path 7*b* between the third on-off valve 16C and the fourth on-off valve 16D and is continuous from the pump 14 to the pressing cuff 71.

In the fluid circuit 7 with such a configuration, by the second on-off valve 16B and the third on-off valve 16C being open and the first on-off valve 16A and the fourth on-off valve 16D being closed, the third flow path 7*c* and the fourth flow path 7*d* branching from the second flow path 7*b* are connected to the pump 14, and the pump 14, the pressing cuff 71, and the tensile cuff 74 are fluidly connected.

In the fluid circuit 7, by the first on-off valve 16A, the second on-off valve 16B, and the third on-off valve 16C being open and the fourth on-off valve 16D being closed, the first flow path 7*a* and the third flow path 7*c* and the fourth flow path 7*d* branching from the second flow path 7*b* are connected to the pump 14, and the pump 14, the pressing cuff 71, and the tensile cuff 74 and the pump 14 and the sensing cuff 73 are fluidly connected. In the fluid circuit 7, by the second on-off valve 16B, the third on-off valve 16C, and the fourth on-off valve 16D being open and the first on-off valve 16A being closed, the second flow path 7*b*, the third flow path 7*c*, and the fourth flow path 7*d* are connected to the pump 14, and the pump 14, the pressing cuff 71, the tensile cuff 74, and the atmosphere are fluidly connected. In the fluid circuit 7, by the first on-off valve 16A, the second on-off valve 16B, the third on-off valve 16C, and the fourth on-off valve 16D being open, the first flow path 7*a*, the second flow path 7*b*, the third flow path 7*c*, and the fourth flow path 7*d* are connected to the pump 14, and the pump 14, the pressing cuff 71, the sensing cuff 73, the tensile cuff 74, and the atmosphere are fluidly connected.

As illustrated in FIGS. 2, 9, and 14, the power feeding unit 8 is provided in the recess 5*c* formed in the outer surface of the curler 5 on the first end side that protrudes from the device body 3. For example, the power feeding unit 8 is configured to be capable to connect to a connector provided on a charging cable of a charger.

As illustrated in FIGS. 2, 9, and 14, the power feeding unit 8 is provided with a wiring portion 8*a*, the power feeding terminal 8*b*, and a cover 8*c* that covers the wiring portion 8*a* disposed in the recess 5*c* of the curler 5. The first end of the wiring portion 8*a* is connected to the power feeding terminal 8*b*, and the second end is connected to the control unit 55. The power feeding terminal 8*b* is constituted by two circular terminals, for example. For example, the wiring portion 8*a* and the power feeding terminal 8*b* are formed of flexible printed circuits (FPC) and the like including a base film, such as polyimide, provided with an electrically conductive metal film and the like. The cover 8*c* is formed in the same shape as the recess 5*c* and covering the recess 5*c*, and the upper surface runs flush with the outer surface of the curler 5 on the shorter side when the cover 8*c* is provided in the recess 5*c*.

Next, an example of a method for manufacturing the blood pressure measurement device 1 will be described using FIG. 26.

First, the power feeding unit 8 is formed on the curler 5 (step ST11). The FPC constituting the wiring portion 8*a* and the power feeding terminal 8*b* is joined to the cover portion 5*a* and the recess 5*c* of the curler 5 by double-sided tape or the like and the cover 8*c* is joined to the recess 5*c* by double-sided tape of the like.

Next, the cuff structure 6 is joined to the curler 5 (step ST12). In a specific example, first, the back plate 72 is disposed in a jig for curving and heated in a heating furnace to heat treat the back plate 72 and curve it in a predetermined shape. Next, the joining layer 75, i.e., double-sided tape, is attached to a region of the fourth sheet member 86*d* of the pressing cuff 71 facing the curler 5 and the target join portion 82, and the pressing cuff 71 is attached to the curler 5. Then, double-sided tape is attached to the region of the sixth sheet member 96*b* of the sensing cuff 73 facing the back plate 72, and the sensing cuff 73 is attached to the back plate 72. Note that in these steps, the connection portion 84 of the pressing cuff 71 and the connection portion 93 of the sensing cuff 73 are inserted into the first hole portion 5*f*1 and the second hole portion 5*f*2 of the cover portion 5*a* of the curler 5.

Next, double-sided tape is attached to the region of the back plate 72 facing the pressing cuff 71, and the back plate 72 is attached to the first sheet member 86*a* of the pressing cuff 71. Then, double-sided tape is attached to the region of the eighteenth sheet member 106*l* of the tensile cuff 74 facing the curler 5 and the target join portion 102, and the tensile cuff 74 is attached to the curler 5 as well as the flow path body 83 of the pressing cuff 71 disposed on the inner surface of the curler 5 and the flow path body 92 of the sensing cuff 73. These steps join the cuff structure 6 to the curler 5.

Next, the first sealing member 36 and the rear cover 35 are disposed on the cover portion 5*a* and the rear cover 35 is fixed to the cover portion 5*a* with the first joining members 35*a* (step ST13) to constitute a rear lid.

Then, the device body 3 is integrally assembled except for the rear cover 35 (step ST14). In a specific example, first, the second sealing member 37 is formed by insert molding in the base portion 33. Next, the component to be fixed to the base portion 33 is fixed to the base portion 33. For example, the pump 14 is fixed to the base portion 33 by double-sided tape. The first on-off valve 16A, the second on-off valve 16B, the third on-off valve 16C, the fourth on-off valve 16D, the first pressure sensor 17A, and the second pressure sensor 17B are installed in the flow path portion 15. The first tube, the second tube, and the third tube are fixed to the on-off valves 16 and the base portion 33. The first tube, the second tube, and the third tube constitute a portion of the flow path portion 15.

Next, the windshield 32 is attached to the outer case 31. The base portion 33 is then inserted from the opening on the rear cover 35 side of the outer case 31. At this time, for example, the base portion 33 is pressed to inside the sealing groove 31*e* until the end surface 33*c* on the windshield 32 side of the first protrusion portion 33*b* of the base portion 33 abuts on the end surface 31*e*1 of the sealing groove 31*e* of the outer case 31.

When the base portion 33 is inserted inside the outer case 31, the intermediate portion 37*b* and the surrounding region of the second sealing member 37 abut on the inner circumferential surface 31*e*2 of the sealing groove 31*e* of the outer case 31. And thus the second sealing member 37 is pressed toward the center region of the outer case 31 and deformed. This deformation causes the second sealing member 37 to come into close contact with the inner circumferential surface 31*d*.

Next, the power supply unit 18 is fixed to the pump 14 by double-sided tape. After completing these steps, the assembly of the device body 3 is complete.

Next, the rear cover 35 is disposed on the end portion on the wrist 200 side of the outer case 31 of the device body 3, and the outer case 31 and the rear cover 35 are fixed with the second joining members 35*b* (step ST15).

Because the second joining members 35*b* are screws, the rear cover 35 is pressed to the windshield 32 side by the second joining members 35*b* being screwed into the screw holes 31*c* by using a screwdriver and the like. Accordingly, the edge portion 35*f* of the rear cover 35 presses the end surface 37*e* of the second sealing member 37 to the windshield 32 side and deforms the end surface 37*e*, and thus the edge portion 35*f* abuts on the end surface 31*f* of the outer case 31 and the end surface 33*e* of the first protrusion portion 33*b*. Furthermore, by the second sealing member 37 being deformed by this pressing, the second sealing member 37 is pressed against the inner circumferential surface 31*e*2 of the sealing groove 31*e* of the outer case 31 and is further put into close contact with the inner circumferential surface 31*e*2.

In addition, the end surface 33*c* of the base portion 33 abuts on the end surface 31*e*1 of the outer case 31, and the edge portion 35*f* of the rear cover 35 abuts on the end surface 31*f* on the wrist 200 side of the outer case 31 and the end surface 33*e* on the wrist 200 side of the base portion 33. This allows the base portion 33 and the rear cover 35 to be aligned with respect to the outer case 31.

Then, the first belt 61 and the second belt 62 are assembled on the outer case 31 (step ST16). With these steps, the blood pressure measurement device 1 is manufactured. Note that, after manufacturing the blood pressure measurement device 1, adjustments of various parameters in the device body, an appearance inspection, a leak inspection and the like are performed. And the blood pressure measurement device 1 is engraved with a serial number and the like, and packed in an individual box and the like, and thus the blood pressure measurement device 1 is in a shipment state.

Next, an example of measurement of a blood pressure value using the blood pressure measurement device 1 will be described using FIGS. 27 to 30. FIG. 27 is a flowchart illustrating an example of a blood pressure measurement using the blood pressure measurement device 1, illustrating both an operation of a user and an operation of the control unit 55. Additionally, FIGS. 28 to 30 illustrate an example of the user wearing the blood pressure measurement device 1 on the wrist 200.

First, the user attaches the blood pressure measurement device 1 to the wrist 200 (step ST21). As a specific example, for example, the user inserts one of the wrists 200 into the curler 5, as illustrated in FIG. 28.

At this time, in the blood pressure measurement device 1, the device body 3 and the sensing cuff 73 are disposed at opposite positions in the curler 5, and thus the sensing cuff 73 is disposed in a region on the hand palm-side of the wrist 200 in which the artery 210 resides. Thus, the device body 3 and the tensile cuff 74 are disposed on the hand back side of the wrist 200. Then, as illustrated in FIG. 29, the user passes the second belt 62 through the frame body 61*e* of the buckle 61*b* of the first belt 61 with the hand opposite to the hand on which the blood pressure measurement device 1 is disposed. The user then pulls the second belt 62 to bring the member on the inner circumferential surface side of the curler 5, that is, the cuff structure 6, into close contact with the wrist 200, and inserts the prong 61*f* into one of the small holes 62*a*. Thus, as illustrated in FIGS. 5 and 31, the first belt 61 and the second belt 62 are connected, and the blood pressure measurement device 1 is attached to the wrist 200.

Next, the user operates the operation unit 13 and inputs an instruction corresponding to the start of measurement of the blood pressure value. The operation unit 13 on which an input operation of the instruction has been performed, outputs an electrical signal corresponding to the start of the measurement to the control unit 55 (step ST22). The control unit 55 receives the electrical signal, and then for example, opens the first on-off valve 16A, the second on-off valve 16B, and the third on-off valve 16C, closes the fourth on-off valve 16D, and drives the pump 14 to supply compressed air to the pressing cuff 71, the sensing cuff 73, and the tensile cuff 74 through the first flow path 7*a*, the second flow path 7*b*, the third flow path 7*c*, and the fourth flow path 7*d* (step ST23). Thus, the pressing cuff 71, the sensing cuff 73, and the tensile cuff 74 start to be inflated.

The first pressure sensor 17A and the second pressure sensor 17B detect the pressures in the pressing cuff 71, the sensing cuff 73, and the tensile cuff 74, and output, to the control unit 55, electrical signals corresponding to the pressures (step ST24). On the basis of the received electrical signals, the control unit 55 determines whether the pressures in the internal spaces of the pressing cuff 71, the sensing cuff 73, and the tensile cuff 74 have reached a predetermined pressure for measurement of the blood pressure (step ST25). For example, in a case where the internal pressures of the pressing cuff 71 and the tensile cuff 74 have not reached the predetermined pressure and the internal pressure of the sensing cuff 73 has reached the predetermined pressure, the control unit 55 closes the first on-off valve 16A and supplies the compressed air through the second flow path 7*b*, the third flow path 7*c*, and the fourth flow path 7*d*.

When the internal pressures of the pressing cuff 71 and the tensile cuff 74 and the internal pressure of the sensing cuff 73 all have reached the predetermined pressure, the control unit 55 stops driving the pump 14 (YES in step ST25). At this time, as illustrated by the two-dot chain line in FIG. 5, the pressing cuff 71 and the tensile cuff 74 are sufficiently inflated, and the inflated pressing cuff 71 presses the back plate 72. Additionally, the tensile cuff 74 presses against the curler 5 in a direction away from the wrist 200, and then the belt 4, the curler 5, and the device body 3 move in a direction away from the wrist 200, and as a result, the pressing cuff 71, the back plate 72, and the sensing cuff 73 are pulled toward the wrist 200 side. In addition, when the belt 4, the curler 5, and the device body 3 move in a direction away from the wrist 200 due to the inflation of the tensile cuff 74, the belt 4 and the curler 5 move toward both lateral sides of the wrist 200, and the belt 4, the curler 5, and the device body 3 move in a state of close contact with both lateral sides of the wrist 200. Thus, the belt 4 and the curler 5, which are in close contact with the skin of the wrist 200, pull the skin on both lateral sides of the wrist 200 toward the hand back side. Note that the curler 5 may be configured to indirectly contact the skin of the wrist 200 with the sheet members 86 or 106 in between, for example, as long as the curler 5 can pull the skin of the wrist 200.

Furthermore, the sensing cuff 73 is inflated by being supplied with a predetermined amount of air such that the internal pressure equals the pressure required to measure blood pressure, and is pressed toward the wrist 200 by the back plate 72 that is pressed by the pressing cuff 71. Thus, the sensing cuff 73 presses the artery 210 in the wrist 200 and occludes the artery 210 as illustrated in FIG. 31.

Additionally, the control unit 55, for example, controls the third on-off valve 16C and repeats the opening and closing of the third on-off valve 16C, or adjusts the degree of opening of the third on-off valve 16C to pressurize a pressure of the internal space of the pressing cuff 71. In the process of pressurization, based on the electrical signal output by the second pressure sensor 17B, the control unit 55 obtains measurement results such as blood pressure values, for example, the systolic blood pressure and the diastolic blood pressure, and the heart rate and the like (step ST26). The control unit 55 outputs an image signal corresponding to the obtained measurement results to the display unit 12, and displays the measurement results on the display unit 12 (step ST27). In addition, after the end of the blood pressure measurement, the control unit 55 opens the first on-off valve 16A, the second on-off valve 16B, the third on-off valve 16C, and the fourth on-off valve 16D.

The display unit 12 receives the image signal, and then displays the measurement results on the screen. The user views the display unit 12 to confirm the measurement results. After the measurement is complete, the user removes the prong 61*f* from the small hole 62*a*, removes the second belt 62 from the frame body 61*e*, and pulls out the wrist 200 from the curler 5, thus detaching the blood pressure measurement device 1 from the wrist 200.

The blood pressure measurement device 1 according to an embodiment with such a configuration is configured to include the first sealing member 36 and the second sealing member 37. This gives the blood pressure measurement device 1 high sealing properties. Furthermore, with the two level structure including the first sealing member 36 and the second sealing member 37 functioning as a waterproof structure for inside the case 11, the sealing property required for the blood pressure measurement device 1 can be satisfied by the combined sealing properties of the first sealing member 36 and the second sealing member 37, allowing the individual sealing properties of the first sealing member 36 and the second sealing member 37 to be set not as high.

Thus, the first sealing member 36 and the second sealing member 37 are not made as a seal with a complex mechanism, for example. As a result, the curler 5 is made easy to detach from the rear cover 35, allowing the cuff structure 6 to be replaceable. Furthermore, even when the curler 5 is detached from the rear cover 35 for maintenance or cuff replacement, only the seal of the first sealing member 36 needs to be removed. "Removing the seal of the first sealing member 36" here refers to detaching the first sealing member 36 or breaking a portion of the first sealing member 36, for example. In the present embodiment, the first sealing member 36 is configured to be formed from adhesive tape, and thus the first sealing member 36 is peeled off from the rear cover 35 or the curler 5.

Furthermore, even in a case where, after breaking the seal, the first sealing member 36 needs to be replaced, the cost of the replacement can be kept low.

Also, because the base portion 33 abuts on the end surface **31*e*1 of the outer case 31 in the axial direction D of the outer case 31, misalignment of the outer case 31 and the base portion 33** can be prevented.

Furthermore, because the first sealing member 36 is constituted by a double-sided tape, the first sealing member 36 can be given a simple configuration. Also, the first sealing member 36 itself, by fixing the curler 5 to the rear cover 35, allows the curler 5 and the rear cover 35 to be strongly fixed. Furthermore, the replacement work of the first sealing member 36 can be made simple, and the cost of replacing the first sealing member 36 can be kept low.

The second sealing member 37 is formed by insert molding, for example, and integrally formed with the base portion 33. Thus, the second sealing member 37 can be prevented from falling out from the base portion 33. Furthermore, as in the present embodiment, even in a case where the inner circumferential surface of the outer case 31 is not a perfect circle, but a portion of the inner circumferential surface is constituted in a flat surface and the other portion of the inner circumferential surface is constituted in a curved surface, the second sealing member 37 is integrally formed with the base portion 33, and the second sealing member 37 is integrally disposed with the base portion 33 inside the outer case 31, and thus the work of detaching the second sealing member 37 is made easy.

Furthermore, the diameter of the intermediate portion **37*b* of the outer circumferential surface 37*a* of the second sealing member 37, when the second sealing member 37 is in a state before being housed inside the sealing groove 31*e*, is greater than the diameter of the inner circumferential surface 31*e*2 of the sealing groove 31*e*. Thus, the second sealing member 37 is squashed in the radial direction when housed in the sealing groove 31*e* and comes into close contact with the inner circumferential surface 31*e*2. In this manner, the sealing property of the second sealing member 37** can be improved.

Furthermore, the region **37*c* of the outer circumferential surface of the second sealing member 37, when the second sealing member 37 is in a state before being deformed, is constituted as a surface that progressively decreases in diameter from the intermediate portion 37*b*, and the diameter of the end on the windshield 32 side of the outer circumferential surface of the second sealing member 37 is less than the diameter of the opening on the wrist 200 side of the sealing groove 31*e*. Thus, when the base portion 33 is moved to inside the outer case 31, the second sealing member 37 can be smoothly housed in the sealing groove 31*e*, and the region 37*c* abuts on the opening of the sealing groove 31*e*, acting as a guide, allowing for smooth movement of the base portion 33 to inside the outer case 31. Furthermore, this can help prevent the second sealing member 37 getting caught on the opening edge of the sealing groove 31*e* of the outer case 31, thus preventing the second sealing member 37 from falling out from the base portion 33**.

Also, the outer circumference surface **33*a* of the base portion 33 includes the second protrusion portion 33*d* disposed inside the second sealing member 37. This helps to further prevent the second sealing member 37 from falling out from the base portion 33**.

Furthermore, the intermediate portion in the radial direction of the end surface **37*e* of the second sealing member 37 is constituted in a shape protruding toward the wrist 200 side. Thus, even in a case where the second sealing member 37 is pressed and deformed by the rear cover 35, the second sealing member 37 can be prevented from being caught between the rear cover 35 and the end surface 31*f* of the outer case 31**.

Note that the present invention is not limited to the embodiments described above. In the example described above, the configuration is described in which the end surface **37*d* on the windshield 32 side of the second sealing member 37 is constituted on the same plane as the end surface 33*c* of the first protrusion portion 33*b* of the base portion 33. However, no such limitation is intended. For example, as illustrated by the two-dot dash line in FIG. 32 of the second sealing member 37 before deformation, the end surface 37*d* on the windshield side of the second sealing member 37 may be constituted in a protruding shape, which protrudes toward the windshield 32 side and is pressed by the end surface 31*e*1 of the outer case 31 in a state where the rear cover is in a fixed state. When the end surface 37*d* is pressed by the end surface 31*e*1, the second sealing member 37 is deformed. As a result, the sealing properties between the outer case 31 and the base portion 33** is improved.

That is, the present invention is not limited to the embodiments described above, and various modifications can be made in an implementation stage within a range that does not depart from the gist of the present invention. Furthermore, each of the embodiments may be implemented in combination as appropriate to the extent possible, and in this case, combined effects can be obtained. Also, the embodiments described above include various stages of invention, and various inventions may be extracted by appropriately combining the described plurality of disclosed constituent elements.

REFERENCE SIGNS LIST

1 Blood pressure measurement device
3 Device body
4 Belt
5 Curler
**5*a*** Cover portion
**5*b*** Escape portion
**5*c*** Recess
**5*d*** Insert member
**5*e*** Screw hole
**5*f*** Hole portion
**5*f*1** First hole portion
**5*f*2** Second hole portion
**5*f*3** Third hole portion
6 Cuff structure
7 Fluid circuit
**7*a*** First flow path
**7*b*** Second flow path
**7*c*** Third flow path
**7*d*** Fourth flow path
8 Power feeding unit
**8*a*** Wire portion
**8*b*** Power feeding terminal
**8*c*** Cover
11 Case
12 Display unit
13 Operation unit
14 Pump
15 Flow path portion
16 On-off valve
16A First on-off valve
16B Second on-off valve
16C Third on-off valve
16D Fourth on-off valve

17 Pressure sensor
17A First pressure sensor
17B Second pressure sensor
18 Power supply unit
19 Vibration motor
20 Control substrate
31 Outer case
31*a* Lug
31*b* Spring rod
31*c* Screw hole
31*e* Sealing groove
31*e*1 End surface
31*e*2 Inner circumferential surface
32 Windshield
33 Base portion
33*b* First protrusion portion
33*d* Second protrusion portion
35 Rear cover
35*a* First joining member
35*b* Second joining member
35*c* Hole portion
35*d* Hole portion
36 First sealing member
37 Second sealing member
41 Button
42 Sensor
43 Touch panel
51 Substrate
52 Acceleration sensor
53 Communication unit
54 Storage unit
55 Control unit
56 Main CPU (central processing unit)
57 Sub-CPU
61 First belt
61*a* Belt portion
61*b* Buckle
61*c* First hole portion
61*d* Second hole portion
61*e* Frame body
61*f* Prong
62 Second belt
62*a* Small hole
62*b* Third hole portion
71 Pressing cuff (cuff)
72 Back plate
72*a* Groove
73 Sensing cuff (cuff)
74 Tensile cuff (cuff)
75 Joining layer
81 Bag-like structure (air bag)
81*a* Weld portion
81*b* Weld portion (join portion)
82 Target join portion
83 Flow path body (first flow path body)
83*a* Weld portion
84 Connection portion (first connection portion)
86 Sheet member
86*a* First sheet member (sheet member)
86*a* First sheet member
86*b* Second sheet member (sheet member)
86*b* Second sheet member
86*b*1 Opening
86*c* Third sheet member
86*cl* Opening
86*d* Fourth sheet member
86*d*1 Hole portion
91 Bag-like structure (air bag)
91*a* Weld portion
91*b* Junction margin
92 Flow path body (second flow path body)
92*a* Weld portion
93 Connection portion
96 Sheet member
96*a* Fifth sheet member
96*b* Sixth sheet member
96*b*1 Hole portion
101 Bag-like structure (air bag)
101*a* Weld portion
101*b* Weld portion (join portion)
101*b* Weld portion
102 Target join portion
102*a* Escape portion
103 Connection portion (third connection portion)
106 Sheet member
106*a* Seventh sheet member
106*b* Eighth sheet member
106*b*1 Opening
106*c* Ninth sheet member
106*cl* Opening
106*d* Tenth sheet member
106*d*1 Opening
106*e* Eleventh sheet member
106*e*1 Opening
106*f* Twelfth sheet member
106*f*1 Opening
106*g* Thirteenth sheet member
106*g*1 Opening
106*h* Fourteenth sheet member
106*h*1 Opening
106*i* Fifteenth sheet member
106*i*1 Opening
106*j* Sixteenth sheet member
106*j*1 Opening
106*k* Seventeenth sheet member
106*k*1 Opening
106*l* Eighteenth sheet member
10611 Hole portion
200 Wrist
210 Artery

The invention claimed is:

1. A blood pressure measurement device attachable to a living body, the blood pressure measurement device comprising:

a curler;

a cuff disposed on an inner surface of the curler;

a case including an outer case having a tubular shape and a rear cover fixed to an end portion on a living body side of the outer case and the curler, an open portion of the rear cover facing the curler being open, and the rear cover covering, together with the curler, the end portion on the living body side of the outer case, the outer case also having a sealing groove located at the end portion on the living body side at an inner circumferential surface of the outer case;

a base portion housed in the case;

a first seal provided between a surface of the rear cover surrounding the open portion and facing the curler and a surface of the curler facing the living body side of the case, the first seal being configured to seal between the rear cover and the curler; and a second seal provided at the sealing groove between the inner circumferential surface of the outer case and an outer circumferential surface of the base portion, the second seal being constituted in an annular shape that seals between the inner circumferential surface of the outer case and the outer circumferential surface of the base portion and seals between a surface of the rear cover facing the living body side of the case and the base portion, and the second seal having a higher sealing property than the first seal, wherein the second seal is fixed to the outer circumferential surface of the base portion, wherein a region of the second seal from one end of the second seal on a side opposite the living body side to a midway portion of the second seal has a surface with a diameter that gradually increases from the one end to the midway portion, and an outer diameter of one end on the living body side of the second seal has a diameter that is smaller than an inner diameter of an opening end on the living body side of the sealing groove, and wherein the open portion of the rear cover is covered by the curler, and the first seal has an annular shape such that the first seal surrounds the open portion of the rear cover.

2. The blood pressure measurement device according to claim 1, wherein the outer case includes a first abutting portion; and the base portion includes a second abutting portion configured to abut on the first abutting portion in an axial direction of the outer case.

3. The blood pressure measurement device according to claim 1, wherein the first seal is constituted by a double-sided tape.

4. The blood pressure measurement device according to claim 1, wherein the second seal is integrally formed with the base portion.

5. The blood pressure measurement device according to claim 1, wherein an outer circumferential surface of the second seal in a pre-deformation state has an intermediate portion in an axial direction of the outer case, and the intermediate portion has a larger diameter than other portions of the outer circumferential surface of the second seal.

6. The blood pressure measurement device according to claim 1, wherein the outer circumferential surface of the base portion includes an annular protrusion portion disposed inside the second seal and protruding toward the inner circumferential surface of the outer case.

7. The blood pressure measurement device according to claim 1, wherein an intermediate portion in a radial direction of an end surface on the living body side of the second seal protrudes further to the living body side than an end on the living body side of the outer case, in a state before the rear cover is fixed to the case.

* * * * *